United States Patent
Kataoka et al.

(10) Patent No.: US 9,314,529 B2
(45) Date of Patent: *Apr. 19, 2016

(54) NUCLEIC ACID DELIVERY COMPOSITION AND CARRIER COMPOSITION, PHARMACEUTICAL COMPOSITION USING THE SAME, AND METHOD FOR NUCLEIC ACID DELIVERY

(75) Inventors: Kazunori Kataoka, Tokyo (JP); Takehiko Ishii, Tokyo (JP); Kensuke Osada, Tokyo (JP); Qixian Chen, Tokyo (JP); Keiji Itaka, Tokyo (JP); Satoshi Uchida, Tokyo (JP)

(73) Assignee: The University of Tokyo, Tokyo (JP)

(*) Notice: Subject to any disclaimer, the term of this patent is extended or adjusted under 35 U.S.C. 154(b) by 48 days.

This patent is subject to a terminal disclaimer.

(21) Appl. No.: 13/808,237

(22) PCT Filed: Jul. 11, 2011

(86) PCT No.: PCT/JP2011/065815
§ 371 (c)(1),
(2), (4) Date: Jan. 3, 2013

(87) PCT Pub. No.: WO2012/005376
PCT Pub. Date: Jan. 12, 2012

(65) Prior Publication Data
US 2013/0109743 A1 May 2, 2013

(30) Foreign Application Priority Data
Jul. 9, 2010 (JP) ................................. 2010-157296

(51) Int. Cl.
| | |
|---|---|
| A61K 48/00 | (2006.01) |
| A61K 47/18 | (2006.01) |
| C08G 81/00 | (2006.01) |
| A61K 47/34 | (2006.01) |
| A61K 47/48 | (2006.01) |
| C12N 15/87 | (2006.01) |
| A61K 9/00 | (2006.01) |
| A61K 38/00 | (2006.01) |
| C08G 63/00 | (2006.01) |

(52) U.S. Cl.
CPC ........... *A61K 47/34* (2013.01); *A61K 47/48215* (2013.01); *A61K 47/48315* (2013.01); *A61K 47/48853* (2013.01); *C12N 15/87* (2013.01); *A61K 9/0019* (2013.01); *A61K 9/0073* (2013.01); *A61K 38/00* (2013.01); *C08G 63/00* (2013.01)

(58) Field of Classification Search
CPC ................. C08G 81/00; A61K 9/1075; A61K 47/48315; A61K 47/48323
See application file for complete search history.

(56) References Cited

U.S. PATENT DOCUMENTS

| 8,546,487 B2 * | 10/2013 | Kataoka et al. | 525/54.2 |
| 8,592,385 B2 * | 11/2013 | Kataoka et al. | 514/44 R |
| 2006/0025330 A1 * | 2/2006 | Sakurai et al. | 514/2 |

FOREIGN PATENT DOCUMENTS

| CA | 2 718 003 A1 | 9/2009 | |
| EP | 0 721 776 A1 | 7/1996 | |
| EP | 1 621 569 A1 | 2/2006 | |
| EP | 2 272 897 A1 | 1/2011 | |
| JP | 10-158196 A | 6/1998 | |
| JP | 2004-352972 A | 12/2004 | |
| WO | 2005/078084 A1 | 8/2005 | |
| WO | 2006/085664 A1 | 8/2006 | |
| WO | WO 2009/009025 A1 * | 1/2009 | ............... C12Q 1/68 |

OTHER PUBLICATIONS

Cho et al., Folate Receptor-Mediated Gene Delivery Using Folate-Poly(ethylene glycol)-Poly(L-lysine) Conjugate. Macromol. Biosci. 2005, 5, 512-519.*
Lee et al., Enhancing Transfection Efficiency Using Polyethylene Glycol Grafted Polyethylenimine and Fusogenic Peptide. Biotechnol. Bioprocess Eng. 2001, 6: 269-273.*
Takae et al., PEG-Detachable Polyplex Micelles Based on Disulfide-Linked Block Catiomers as Bioresponsive Nonviral Gene Vectors. J. AM. CHEM. SOC. 2008. 130,6001-6009.*
Lee et al., PEG grafted poly lysine with fusogenic peptide for gene delivery: high transfection efficiency with low cytotoxicity. Journal of Controlled Release 79 (2002) 283-291.*
Trubetskoy et al. Self-assembly of DNA—polymer complexes using template polymerization. Nucleic Acids Research, 1998, vol. 26, No. 18. 4178-4185.*
Bennett et al., J. Drug Targeting, 5, 149 (1997).
Boussif et al., Proc. Natl. Acad. Sci., USA, 92, 7297 (1995).
Debus et al., "Delivery of messenger RNA using poly(ethylene imine)-(ethylene glycol)-copolymer blends for polyplex formation: Biophysical characterization and in vitro transfection properties," Journal of Controlled Release, 2010, vol. 148, pp. 334-343.
Richardson et l., Int. J. Pharm. 178, (1999) 231.
International Search Report, PCT Application No. PCT/JP2011/065815, mail date Aug. 2, 2011, 3 pages.
Extended European Search Report corresponding to EP Application No. 11 80 3707 dated Nov. 24, 2014 (6 pages).

* cited by examiner

*Primary Examiner* — Kevin Hill
*Assistant Examiner* — Arthur S Leonard
(74) *Attorney, Agent, or Firm* — Kilpatrick Townsend & Stockton LLP

(57) ABSTRACT

An excellent nucleic acid delivery composition is provided which has reduced cytotoxicity and improved nucleic acid introduction efficiency and gene expression efficiency. The composition comprises: a block copolymer having an uncharged hydrophilic polymer segment and a cationic polymer segment; a cationic polymer; and a nucleic acid, wherein the mol percentage (B/H ratio) of the cationic groups of the block copolymer to the total cationic groups of the block copolymer and the cationic polymer is between 25% and 90%.

8 Claims, 11 Drawing Sheets

Fig.7
(a)
(b)
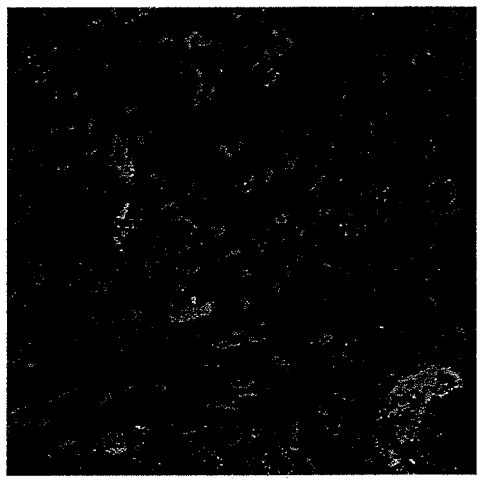 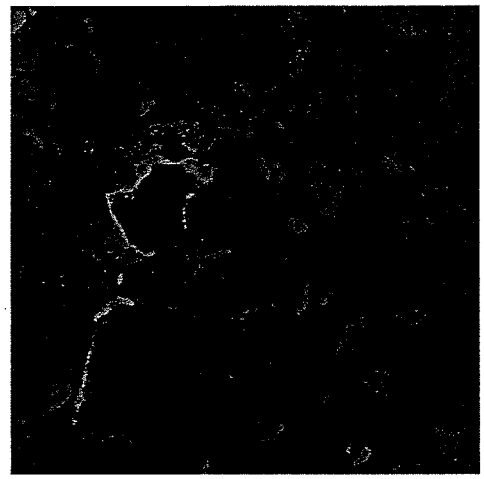
(c)
(d)
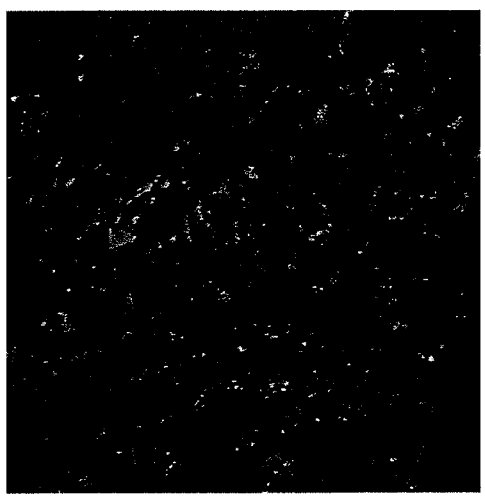 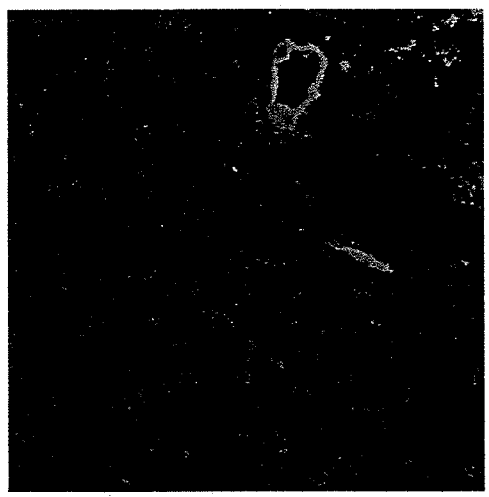

Fig8
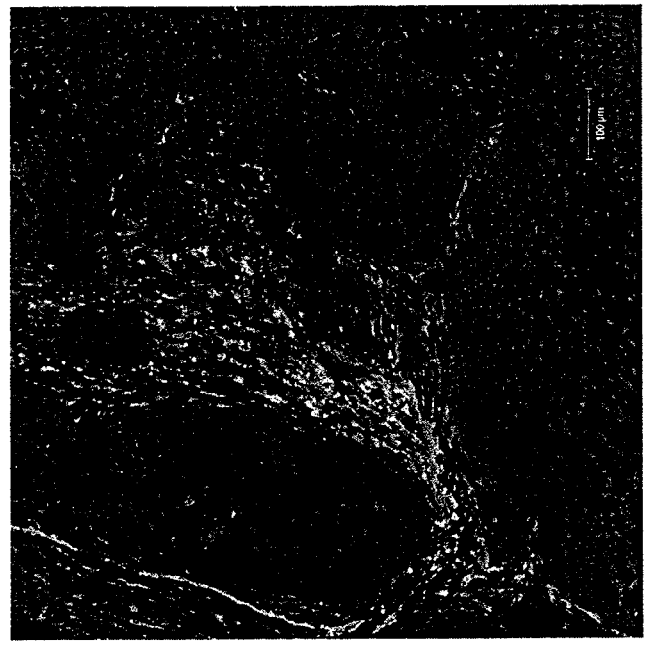
(b)
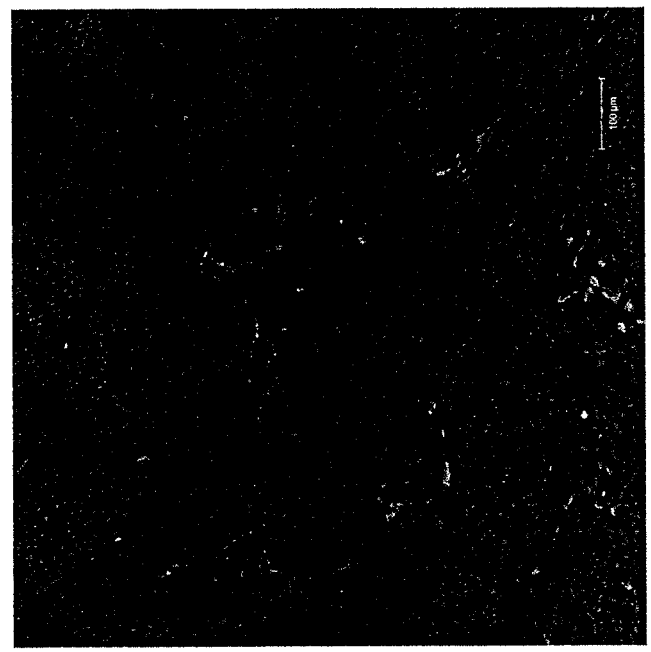
(a)

Fig. 9
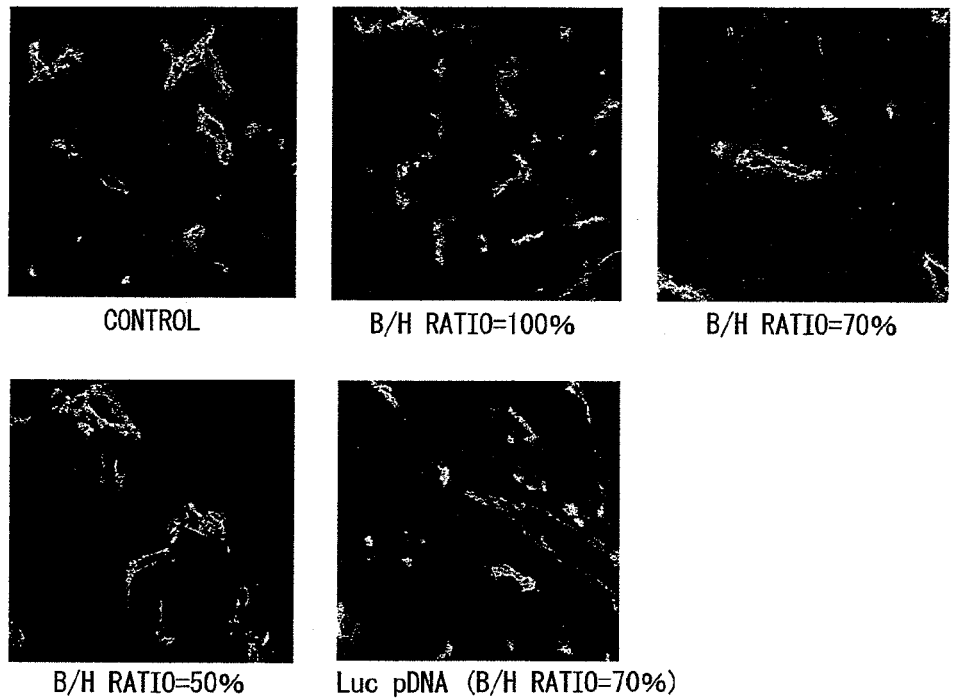
(a)
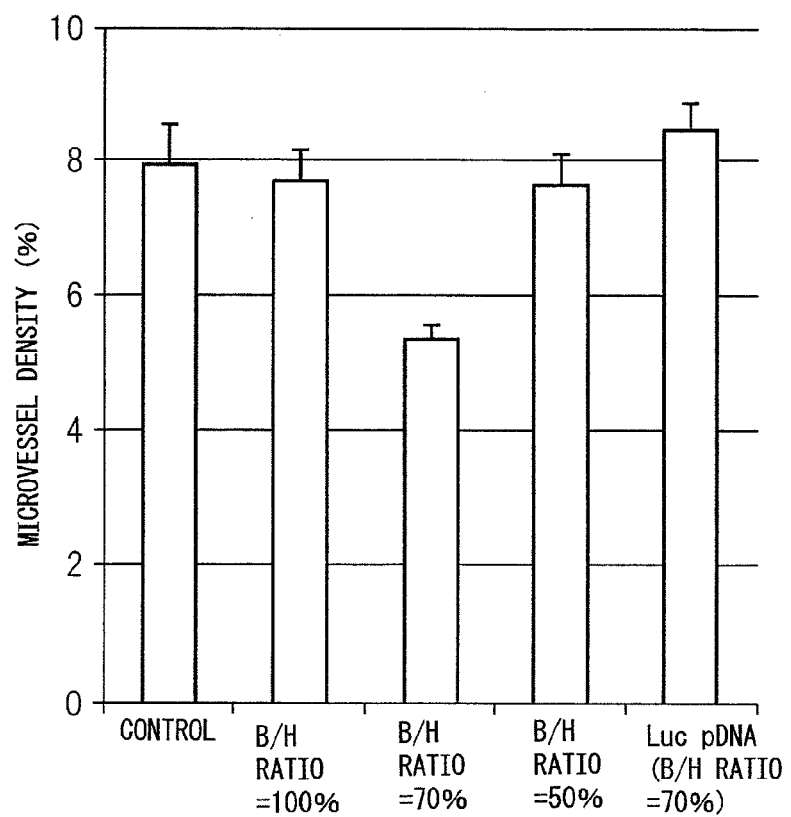
(b)

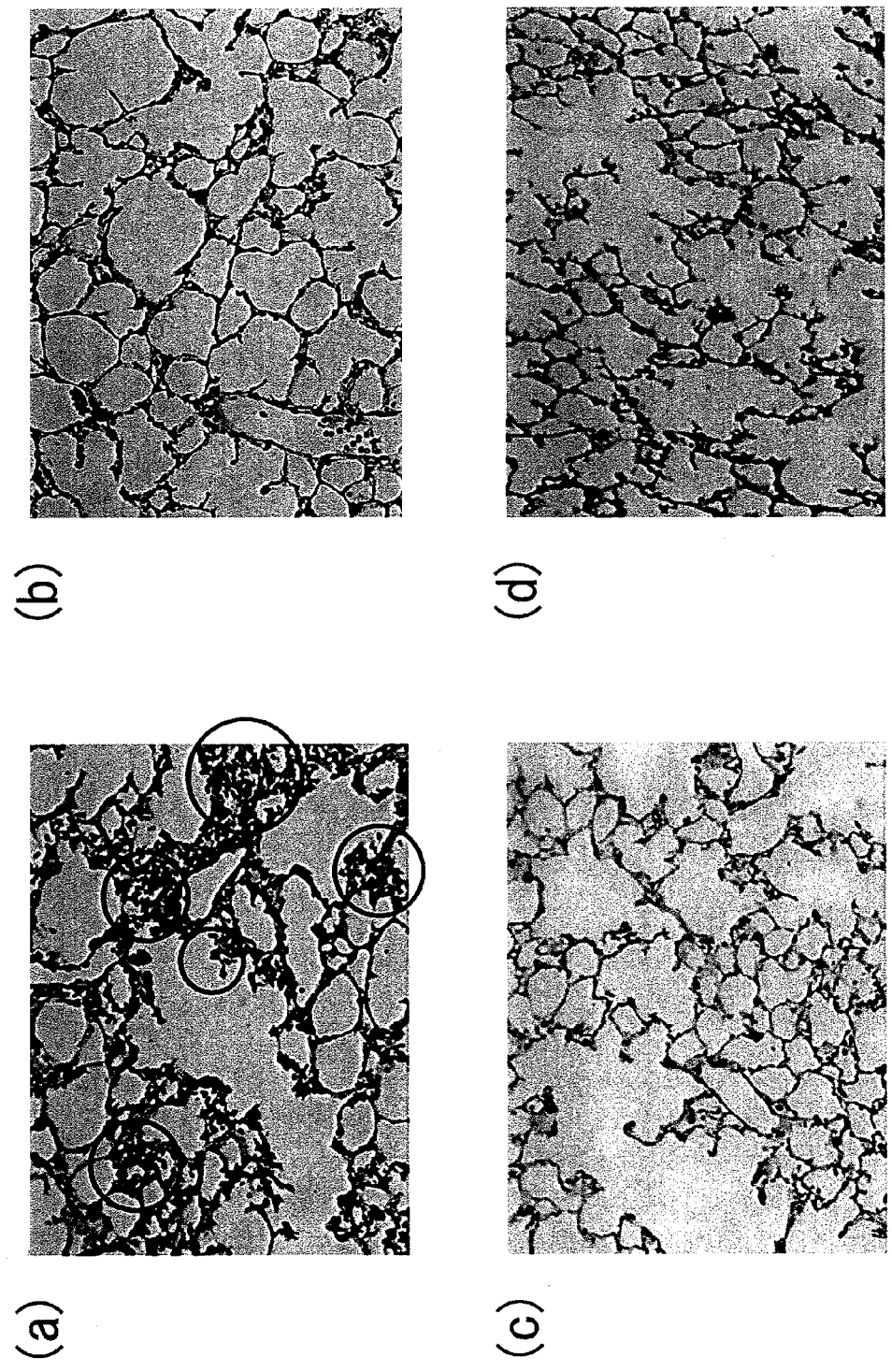

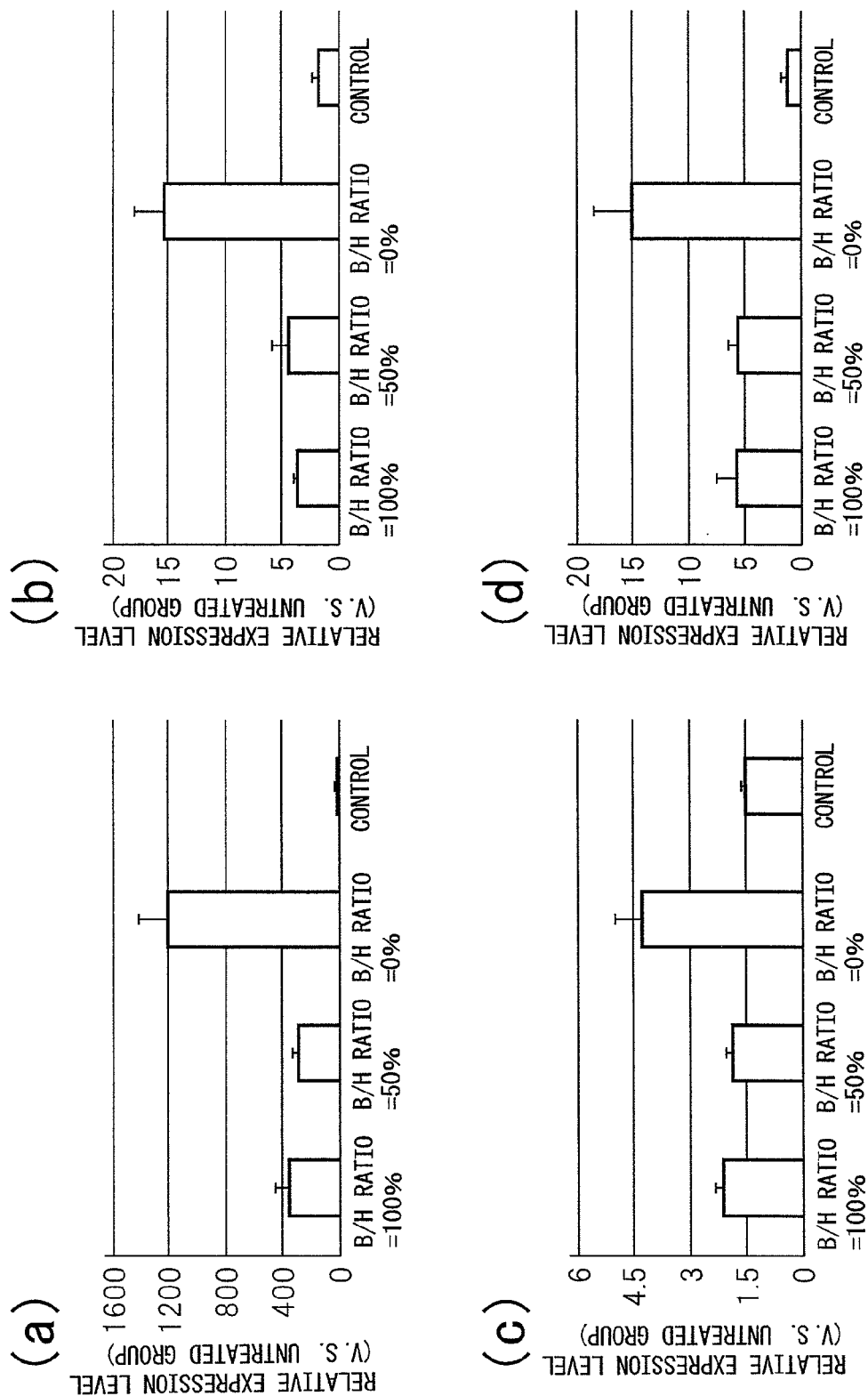

NUCLEIC ACID DELIVERY COMPOSITION AND CARRIER COMPOSITION, PHARMACEUTICAL COMPOSITION USING THE SAME, AND METHOD FOR NUCLEIC ACID DELIVERY

TECHNICAL FIELD

The present invention relates to a nucleic acid delivery composition and a carrier composition, a pharmaceutical composition using the same, as well as a method for nucleic acid delivery, for delivering a nucleic acid to a target cell or tissue.

BACKGROUND ART

In the field of nucleic acid therapy, virus vectors and synthetic carriers (non-viral carriers) have thus far been examined as a carrier for delivering nucleic acids to target cells or a target tissue.

Like drug deliver systems (DDS) that have been examined in the conventional therapy, synthetic carriers involve risks of, e.g., toxicity. Nevertheless, compared to virus vectors, they are considered to be less toxic, have less restriction on the size of nucleic acids to be carried, and allow for more accurate molecular design. Therefore, intense research and development have been made on synthetic carriers.

Typical synthetic carriers include cationic lipids and cationic polymers, which can form an ion complex with DNA, which is negatively charged.

With regard to cationic lipids (e.g., lipofectin), certain positive results have been obtained in vitro (see, e.g., Non-Patent Document 1), although desired results have not necessarily been achieved in vivo.

With regard to cationic polymers, various polymers have been studied, such as poly(L-lysine), DEAE-dextran, polyethyleneimine (see, e.g., Non-Patent Document 2), and chitosan (see, e.g., Non-Patent Document 3). However, these cationic polymers not only have cytotoxicity, but are also insufficient either in nucleic acid introduction efficiency or in gene expression efficiency.

The present inventors have reported that self-assembly of a block copolymer which has a cationic polymer segment containing amine groups on its side chains and an uncharged hydrophilic polymer segment such as polyethylene glycol (PEG) a polyion complex (PIC) yields a polymeric micelle encapsulating a nucleic acid, which exhibits reduced cytotoxicity and shows a certain level of nucleic acid introduction efficiency and gene expression efficiency (see Patent Document 1: JP2004-352972A). However, nucleic acid deliver system using such a PIC polymeric micelle still has room for improvement in nucleic acid introduction efficiency and gene expression efficiency.

The present inventors have also reported that a cationic homopolymer, which contains certain amine groups on its side chains, can be mixed with a nucleic acid to markedly improve nucleic acid introduction efficiency and gene expression efficiency while relatively reducing toxicity on animal cells (especially on mammalian cells) (Patent Document 2: WO2006/085664A). However, nucleic acid deliver system using such a homopolymer still has room for improvement in reduction in cytotoxicity.

PRIOR ART REFERENCES

Patent Documents

Patent Document 1: JP2004-352972A
Patent Document 2: WO2006/085664A

Non-Patent Documents

Non-Patent Document 1: C. F. Benett et al., J. Drug Targeting, 5, 149 (1997)
Non-Patent Document 2: O. Boussif et al., Proc. Natl. Acad. Sci., USA, 92, 7297 (1995)
Non-Patent Document 3: S. C. Richardson et al., Int. J. Pharm. 178, (1999) 231

DISCLOSURE OF THE INVENTION

Problems to be Solved by the Invention

From this background, there is still a demand for an excellent nucleic acid delivery composition which has reduced cytotoxicity and improved nucleic acid introduction efficiency and gene expression efficiency, as well as its carrier therefor.

Means to Solve the Problems

Having made intensive investigations, the present inventors have finally found that an excellent nucleic acid delivery composition with low cytotoxicity and high nucleic acid introduction efficiency can be achieved based on a polyion complex (PIC) polymeric micelle formed of a block copolymer having a certain cationic polymer segment and a certain uncharged hydrophilic polymer segment, by mixing a certain cationic homopolymer therein at a certain ratio, thereby arriving at the present invention.

Thus, an aspect of the present invention resides in a nucleic acid delivery composition for delivering a nucleic acid to a target cell or tissue, comprising: a block copolymer having an uncharged hydrophilic polymer segment and a cationic polymer segment; a cationic polymer; and a nucleic acid, wherein the mol percentage (B/H ratio) of the cationic groups of the block copolymer to the total cationic groups of the block copolymer and the cationic polymer is between 25% and 90%.

Another aspect of the present invention resides in a carrier composition for delivering a nucleic acid to a target cell or tissue, comprising: a block copolymer having an uncharged hydrophilic polymer segment and a cationic polymer segment; and a cationic polymer, wherein the mol percentage (B/H ratio) of the cationic groups of the block copolymer to the total cationic groups of the block copolymer and the cationic polymer is between 25% and 90%.

Still another aspect of the present invention resides in a pharmaceutical composition for use in nucleic acid therapy, comprising a nucleic acid delivery composition or a carrier composition as mentioned above.

Still another aspect of the present invention resides in a method for delivering a nucleic acid to a target cell or tissue, comprising contacting the target cell or tissue with a nucleic acid delivery composition as mentioned above.

Still another aspect of the present invention resides in a method for delivering a nucleic acid to a target cell or tissue, comprising: contacting the target cell or tissue with a nucleic acid delivery composition comprising a block copolymer having an uncharged hydrophilic polymer segment and a cationic polymer segment and a nucleic acid together with a cationic polymer, wherein the mol percentage (B/H ratio) of the cationic groups of the block copolymer to the total cationic groups of the block copolymer and the cationic polymer during the contacting is between 25% and 90%.

Effects of the Invention

The nucleic acid delivery composition and the method for nucleic acid delivery according to the present invention can exhibit superior nucleic acid introduction efficiency while involving only reduced cytotoxicity. In addition, the carrier composition according to the present invention facilitates preparation of such an excellent nucleic acid delivery composition. The nucleic acid delivery composition and the carrier composition according to the present invention are suitable for a pharmaceutical composition for nucleic acid therapy.

BRIEF EXPLANATION OF THE DRAWINGS

FIGS. 7(a) to 7(d) are CLSM (confocal laser scanning microscope) micrograms each showing expression status of Venus in tumor tissue, specifically FIG. 7(a) showing the result of a control, FIG. 7(b) showing the result at a B/H ratio of 100%, FIG. 7(c) showing the result at a B/H ratio of 70%, and FIG. 7(d) showing the result at a B/H ratio of 50%;

FIGS. 8(a) and (b) are CLSM micrograms each showing expression status of sFlt-1 in tumor tissue, specifically FIG. 8(a) showing the result of a control, and FIG. 8(b) showing the result at a B/H ratio of 70%;

FIG. 9(a) indicates CLSM micrograms of immunostained vascular endothelial cells derived from tumor tissue, and FIG. 9(b) is a graph showing vessel density obtained by image analysis of the micrograms of FIG. 9(a);

FIGS. 11(a) to 11(d) are micrograms of immunostained lung tissue, specifically FIG. 11(a) showing the result at a B/H ratio of 100%, FIG. 11(b) showing the result at a B/H ratio of 70%, FIG. 11(c) showing the result at a B/H ratio of 50%, and FIG. 11(d) showing the result of control; and FIGS. 12(a) to 12(d) are graphs each showing the expression level of mRNA, specifically FIG. 12(a) showing the mRNA expression level of IL-6, FIG. 12(b) showing the mRNA expression level of TNF-α, FIG. 12(c) showing the mRNA expression level of Cox-2, and FIG. 12(d) showing the mRNA expression level of IL-10.

MODE FOR CARRYING OUT THE INVENTION

Figure 1:
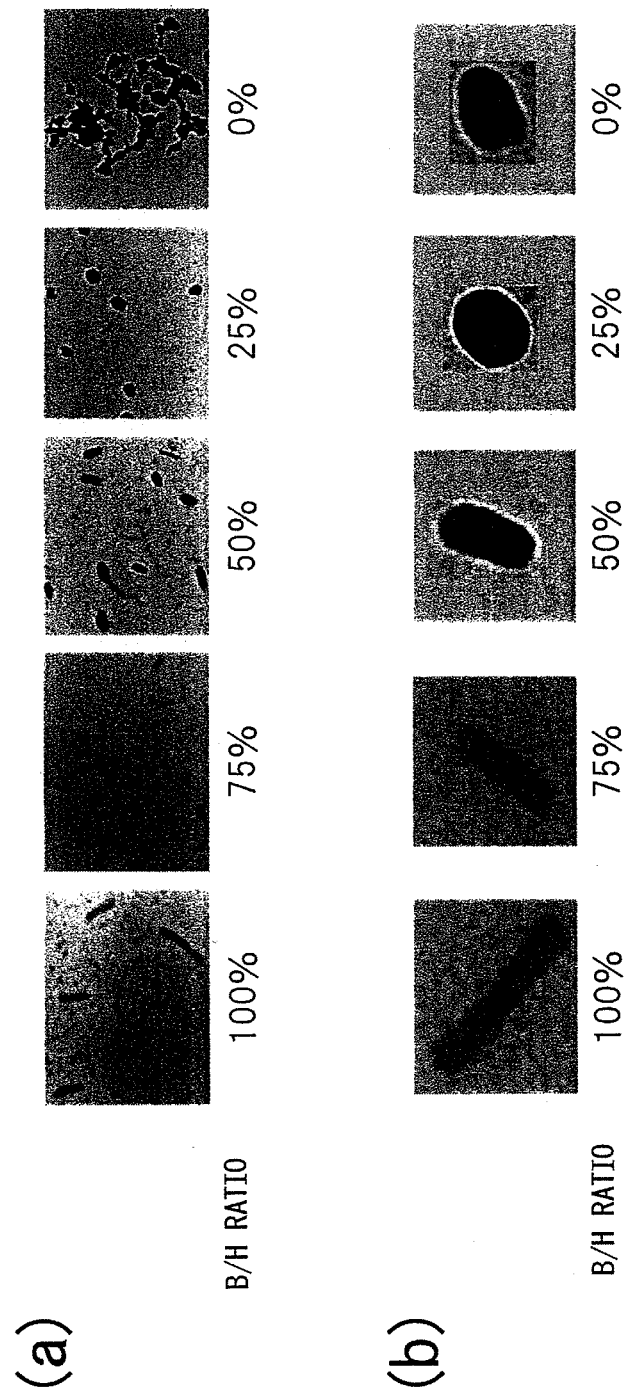
FIGS. 1(a) and 1(b) are transmission electron micrograms showing particle shapes at different B/H ratios.

According to the present invention, a composition for delivering a nucleic acid(s) to a target cell(s) or tissue(s) is provided, wherein together with comprising a specific copolymer, a cationic copolymer and a nucleic acid to be subsequently described, the ratio of the block copolymer to the cationic polymer is within a specific range to be subsequently described (nucleic acid delivery composition of the present invention).

According to studies conducted by the inventors of the present invention, by using a specific block copolymer and cationic polymer to be subsequently described at a ratio such that a B/H ratio to be subsequently described satisfies a specific range, toxicity to animal cells (and particularly mammalian cells) can be suppressed to a low level roughly equal to that of PIC micelle type nucleic acid delivery systems composed of block copolymer alone (such as that described in Patent Document 1), and nucleic acid transfection efficiency can be improved to roughly the same as that of nucleic acid delivery systems using cationic polymer alone (such as that described in Patent Document 2). Namely, according to the present invention, a nucleic acid delivery composition is provided that realizes only the advantages of both conventional nucleic acid delivery systems using only block copolymers and nucleic acid delivery systems using only cationic polymers. The resulting synergistic effects cannot be predicted from simply gathering together findings relating to conventional nucleic acid delivery systems.

In addition, according to the present invention, a carrier composition for delivering a nucleic acid(s) to a target cell(s) or tissue(s) is provided, wherein together with comprising a specific block copolymer, cationic polymer and nucleic acid to be subsequently described, the ratio of the block copolymer to the cationic polymer is within a specific range to be subsequently described (carrier composition of the present invention). The nucleic acid delivery composition of the present invention can be obtained by supporting a nucleic acid on the carrier composition.

[Block Copolymer]

The block copolymer used in the present invention has an uncharged hydrophilic polymer segment and a cationic polymer segment. One type of block copolymer may be used or two or more types may be used in an arbitrary combination and ratio.

(Uncharged Hydrophilic Polymer Segment)

The uncharged hydrophilic polymer segment is a polymer segment that is uncharged and has hydrophilic properties. Here, "uncharged" refers to the segment being neutral overall. An example thereof is the case in which the segment does not have a positive or negative charge. In addition, even in the case the segment has a positive or negative charge within a molecule thereof, as long as the local effective charge density is not high and overall charge of the segment is neutralized to a degree that the formation of polymer micelles is not impaired, this is again equivalent to being "uncharged". In addition, "hydrophilic" indicates solubility with respect to an aqueous medium.

There are no particular limitations on the type of uncharged hydrophilic polymer segment. The segment may be a segment composed of a single repeating unit or a segment containing two or more types of repeating units in an arbitrary combination and ratio. Specific examples of the uncharged hydrophilic polymer segment include polyalkylene glycol, poly(2-oxazoline), polysaccharide, polyvinyl alcohol, polyvinyl pyrrolidone, polyacrylamide, polymethacrylamide, polyacrylic acid ester, polymethacrylic acid ester, poly(2-methacryloyloxyethylphosphorylcholine), peptides and proteins having an isoelectric point in the vicinity of 7, and derivatives thereof. Among these, polyalkylene glycol and poly(2-oxazoline) are preferable, and polyalkylene glycol is particularly preferable. Although examples of polyalkylene glycol include polyethylene glycol and polypropylene glycol, polyethylene glycol (PEG) is preferable.

Although there are no particular limitations on the molecular weight of the uncharged hydrophilic polymer segment, from the viewpoint of efficiently producing polymer micelles, the uncharged hydrophilic polymer segment preferably has a molecular weight within a prescribed range. Although the specific molecular weight range varies depending on the type of uncharged hydrophilic polymer segment, the cationic polymer segment combined therewith and the like, in the case of using polyethylene glycol for the uncharged hydrophilic polymer segment, the molecular weight (Mw) thereof is preferably within the range of 500 or more and more preferably 1000 or more to 40000 or less and more preferably 30000 or less. Although there are also no restrictions on the number of repeating units of the uncharged hydrophilic polymer segment, the number of repeating units is normally determined corresponding to the type of repeating units so that the molecular weight of the uncharged hydrophilic polymer segment satisfies the aforementioned molecular weight range.

The use of an uncharged hydrophilic polymer segment that satisfies the aforementioned conditions makes it possible to stabilize the block copolymer, by preventing association and precipitation thereof in an aqueous solution, and efficiently form polymer micelles capable of functioning as a carrier composition.

(Cationic Polymer Segment)

The cationic polymer segment is a polymer segment that has cationic groups and demonstrates cationic properties (positive ionic properties). However, the cationic polymer segment may also have some anionic groups within a range that does not impair the formation of polymer micelles.

There are also no limitations on the cationic polymer segment. The cationic polymer segment may be composed of a single repeating unit or may contain two or more types of repeating units in an arbitrary combination and ratio. The cationic polymer segment is preferably a polyamine, and particularly preferably a poly(amino acid or derivative thereof) having amino groups in the side chains thereof. Although there are no limitations thereon, examples of amino acids or derivatives thereof that compose this poly(amino acid or derivative thereof) include amino group-containing aspartamide, amino group-containing glutamide, lysine, arginine and histidine. Among these, amino group-containing aspartamide and amino group-containing glutamide are particularly preferable.

Although there are no particular limitations thereon, from the viewpoint of efficiently producing polymer micelles, the molecular weight of the cationic polymer segment preferably has a molecular weight within a prescribed range. Although there are also no restrictions on the number of repeating units of the cationic polymer segment, it is normally determined corresponding to the type of repeating units such that the molecular weight of the cationic polymer segment satisfies a prescribed molecular weight range. More specifically, in the case of using a polyaspartic acid derivative or polyglutamic acid derivative for the cationic polymer segment, the number of repeating units thereof is preferably within the range of 5 or more and more preferably 10 or more to preferably 300 or less and more preferably 200 or less.

The use of a cationic polymer segment that satisfies the aforementioned conditions makes it possible to stabilize the block copolymer, by preventing association and precipitation thereof in an aqueous solution, and efficiently form polymer micelles capable of functioning as a carrier composition.

(Combination of Uncharged Hydrophilic Polymer Segment and Cationic Polymer Segment)

There are no restrictions on the combination of the uncharged hydrophilic polymer segment and the cationic polymer segment, and an arbitrary uncharged hydrophilic polymer segment and an arbitrary cationic polymer segment can be combined.

The numbers of uncharged hydrophilic polymer segments and cationic polymer segments is also arbitrary, and may be one each or two or more each, and in the case of two or more each, the segments may be mutually the same or different. Normally, one cationic polymer segment is preferably bonded to one uncharged hydrophilic polymer segment. However, from the viewpoint of retaining a large amount of nucleic acid in the polymer micelles, a form in which two or more cationic polymer segments are bonded to one uncharged hydrophilic polymer segment is also preferable.

(Linking Group)

There are also no restrictions on the bonding form between the uncharged hydrophilic polymer segment and the cationic polymer segment, and they may be bonded directly or bonded through a linking group.

Examples of linking groups include hydrocarbon groups having a valence corresponding to the total number of uncharged hydrophilic polymer segments and cationic polymer segments. The hydrocarbon group used as a linking group may be aliphatic, aromatic or a linked form thereof, an aliphatic hydrocarbon group may be saturated or unsaturated, and it may be linear or branched. Although there no restrictions thereon, the molecular weight of the hydrocarbon group used as a linking group is normally 5000 or less and preferably 1000 or less. Although examples of hydrocarbon groups used as linking groups include gallic acid derivatives, 3,5-dihydroxybenzoic acid derivatives, glycerin derivatives, cyclohexane derivatives and L-lysine, 3,5-dihydroxybenzoic acid derivatives are preferable.

Other examples of linking groups include disulfide groups. Disulfide groups are used to link one uncharged hydrophilic polymer segment with one cationic polymer segment. As a result of linking the uncharged hydrophilic polymer segment and the cationic polymer segment through a disulfide group, the form and properties of polymer micelles can be changed as a result of the disulfide groups being cleaved by the environment in which the polymer micelles are placed as well as external action. The use thereof is thought to make it possible to promote the site-specific release of a drug (the form of which will be subsequently described) contained within the polymer micelles by cleaving a disulfide group at a specific site in the body.

In addition, although the ratio of the uncharged hydrophilic polymer segment to the cationic polymer segment is also arbitrary, from the viewpoint of efficiently producing polymer micelles, the molecular weight ratio of the uncharged hydrophilic polymer segment contained in the polymer micelles is preferably within a prescribed range. Since the specific ratio is preferably determined in consideration of the amount of nucleic acid, it will be subsequently described in the section on "Nucleic Acid".

(Specific Examples of Block Copolymer)

Preferable specific examples of the block copolymer of the present invention include block copolymers represented by the following formulae (I) to (IV) that have a polyethylene glycol (PEG) segment for the uncharged hydrophilic polymer segment and a poly(amino acid or derivative thereof) segment for the cationic polymer segment.

[Chemical Formula 1]

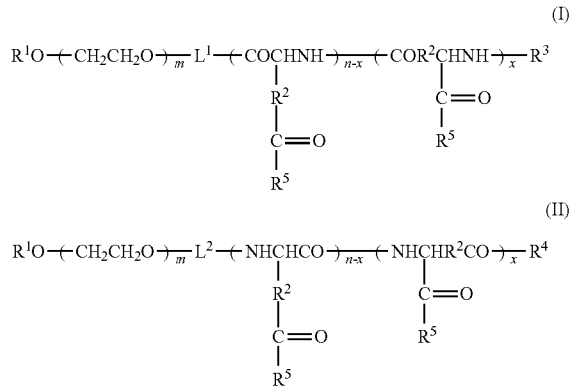

In formulae (I) and (II), $R^1$ represents a hydrogen atom or unsubstituted or substituted, linear or branched $C_{1-12}$ alkyl group, $R^2$ represents a methylene group or ethylene group, $R^3$ represents a hydrogen atom, protecting group, hydrophobic group or polymerizable group, $R^4$ is either the same as $R^5$ or represents an initiator residue, $R^5$ respectively and independently represent a hydroxyl group, oxybenzyl group or —NH—$(CH_2)_a$—X group, X respectively and independently represents a bulky amine compound residue having a pKa value of 7.4 or less, an amine compound residue containing one type or two or more types of a primary, secondary, tertiary or quaternary amine, or a non-amine compound residue, $L^1$ and $L^2$ respectively and independently represent a linking group, a represents an integer of 1 to 5, m represents an integer of 5 to 20,000, n represents an integer of 2 to 5,000, and x represents an integer of 0 to 5,000, provided that x is not greater than n.

X respectively and independently represents a bulky amine compound residue having a pKa value of 7.4 or less, an amine compound residue containing one type or two or more types of a primary, secondary, tertiary or quaternary amine, or a non-amine compound residue, $L^1$ and $L^2$ respectively and independently represent a linking group, a represents an integer of 1 to 5, $R^6$ respectively and independently represents a hydrogen atom or protecting group, m represents an integer of 5 to 20,000, n represents an integer of 2 to 5,000, y represents an integer of 0 to 5,000 and z represents an integer of 0 to 5,000, provided that y+z is not greater than n.

Detailed definitions of each group in the aforementioned formulae (I) to (IV) are as indicated below.

Although $R^1$ represents a hydrogen atom or unsubstituted or substituted, linear or branched $C_{1-12}$ alkyl group, examples of $C_{1-12}$ alkyl groups include a methyl group, ethyl group, n-propyl group, isopropyl group, n-butyl group, sec-butyl group, tert-butyl group, n-pentyl group, n-hexyl group, decyl group and undecyl group. Examples of substituents in the case the $C_{1-12}$ alkyl group is substituted include an acetalated formyl group, cyano group, formyl group, carboxyl group, amino group, $C_{1-6}$ alkoxycarbonyl group, $C_{2-7}$ acylamido group, tri-$C_{1-6}$ alkylsiloxy group (wherein, the three alkyl groups may be the same or different), siloxy group and silylamino group.

In the case the aforementioned substituent is an acetalated formyl group, it can be converted to another substituent in the form of a formyl group (—CHO: aldehyde group) by hydrolyzing under mildly acidic conditions. In the case the formyl group, carboxyl group or amino group is present in the vicinity of the outer edge of the polymer micelles, it can be used to covalently bond a protein and the like to the polymer micelles through that group. Examples of proteins and the like include antibodies or specifically bonding fragments thereof (such as F(ab')2 or F(ab)) and other proteins able to impart their func-

[Chemical Formula 2]

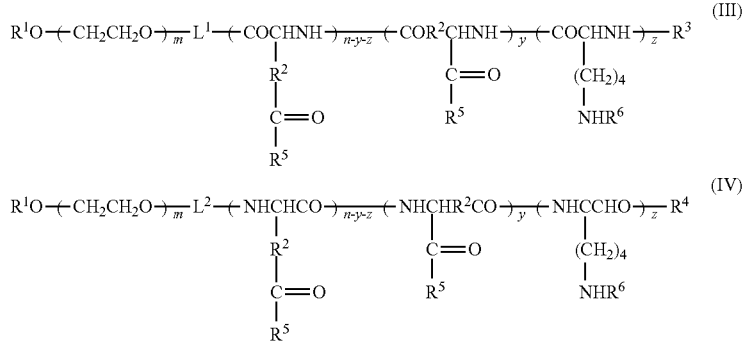

In formulae (III) and (IV), $R^1$ represents a hydrogen atom or unsubstituted or substituted, linear or branched $C_{1-12}$ alkyl group, $R^2$ represents a methylene group or ethylene group, $R^3$ represents a hydrogen atom, protecting group, hydrophobic group or polymerizable group, $R^4$ is either the same as $R^5$ or represents an initiator residue, $R^5$ respectively and independently represent a hydroxyl group, oxybenzyl group or —NH—$(CH_2)_a$—X group, tion or target orientation to polymer micelles. Examples of methods used to produce PEG segments having such functional groups on one end thereof include block copolymer PEG segment production methods described in WO 96/32434, WO 96/33233 and WO 97/06202.

$R^2$ represents a methylene group or ethylene group. A repeating unit of the poly(amino acid or derivative thereof) segment that contains $R^2$ is equivalent to an aspartic acid derivative unit in the case $R^2$ represents a methylene group, or is equivalent to a glutamic acid derivative unit in the case $R^2$ represents an ethylene group. In the case the poly(amino acid or derivative thereof) segment has both a methylene group and ethylene group for $R^2$, the aspartic acid derivative unit and the glutamic acid derivative unit may be respectively and independently present and form blocks, or may be randomly mixed.

$R^3$ represents a hydrogen atom, protecting group, hydrophobic group or polymerizable group. An example of a protecting group is a $C_{1-6}$ alkylcarbonyl group, and is preferably an acetyl group. Examples of hydrophobic groups include a benzene group, naphthalene group, anthracene group and pyrene group. Examples of polymerizable groups include a methacryloyl group and acryloyl group. In the case the copolymer of general formula (I) or (III) has a polymerizable group, the copolymer can be used as a so-called macromer. For example, after having formed a polymer micelle, the polymer micelle can be crosslinked through these polymerizable groups using another comonomer as necessary.

$R^4$ represents a hydroxyl group, oxybenzyl group or —NH—$(CH_2)_a$—X group in the same manner as $R^5$, or represents an initiator residue. The case of $R^4$ being an initiator residue refers to the case of adopting a structure derived from an initiator in which $R^4$ was used in the case of producing a block copolymer represented by general formulae (I) to (IV) by the second method to be subsequently described (namely, a method in which a PEG segment is bonded after having synthesized a poly(amino acid or derivative thereof) segment by polymerizing an NCA of a protective amino acid using a low molecular weight initiator). A specific example of an initiator residue is —NH—$R^9$. Here, $R^9$ represents an unsubstituted or substituted, linear or branched $C_{1-20}$ alkyl group.

Although $R^5$ respectively and independently represents a hydroxyl group, oxybenzyl group or —NH—$(CH_2)_a$—X group, the majority thereof (normally 85% or more, preferably 95% or more, more preferably 98% or more and particularly preferably 100%) is an —NH—$(CH_2)_a$—X group.

Although there are no restrictions on X provided the block copolymer satisfies the conditions of the present invention (or coincides with the object of the present invention), it is normally selected from the residues classified into one of the following groups A to E.

*Group A: Bulky amine compound residue having pKa value of 7.4 or less:

[Chemical Formula 3]

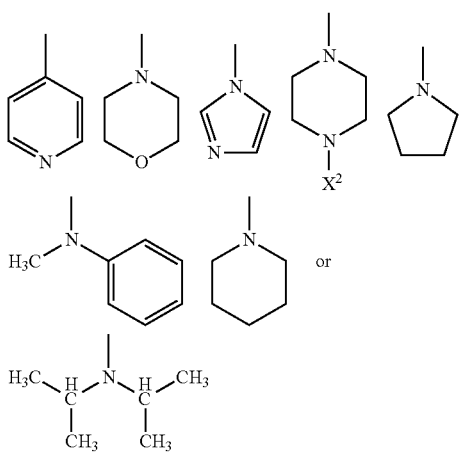

In group A, $X^2$ represents a hydrogen atom or $C_{1-6}$ alkyl group.

*Group B: Amine compound residue containing both a primary amine and a secondary amine, tertiary amine or quaternary amine:

[Chemical Formula 4]

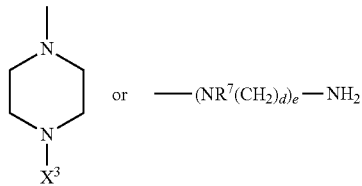

In group B, $X^3$ represents an amino-$C_{1-6}$ alkyl group, $R^7$ represents a hydrogen atom or methyl group, and d and e respectively and independently represent an integer of 1 to 5.

*Group C: Amine compound residue containing only a primary amine:

—$(CH_2)_f$—$NH_2$     [Chemical Formula 5]

In group C, f represents an integer of 0 to 15.

*Group D: Amine compound residue containing only a secondary amine, tertiary amine or quaternary ammonium salt that is not included in group A:

—$(NR^7(CH_2)_d)_e$—$NHR^8$—$N(CH_3)_2$ or
—$N(CH_2CH_3)_2$     [Chemical Formula 6]

In group D, d and e respectively and independently represent an integer of 1 to 5, and $R^8$ represents a protecting group such as a Z group, Boc group, acetyl group or trifluoroacetyl group.

*Group E: Non-amine compound residue:

[Chemical Formula 7]

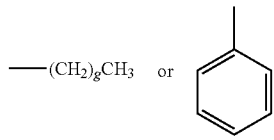

In group E, g represents an integer of 0 to 15.

In the case of a block copolymer represented by general formula (I) or (II), although the block copolymer may contain any one residue selected from the residues of group A and group B for X, group C must simultaneously contain at least one residue selected from the residues of group A and group D, and group D must simultaneously contain at least one residue selected from the residues of group B and group C. In addition, although group E can be contained in order to change the physical properties of the copolymer, the aforementioned conditions must be satisfied by the portion excluding group E.

In the case of a block copolymer represented by general formula (III) or (IV), if at least one of $R^6$ is a hydrogen atom, only residue selected from the residues of group A, group B and group D may be contained. The conditions for group C and group E are the same as those described above.

Although $R^6$ respectively and independently represents a hydrogen atom or protecting group, the majority thereof (normally 85% or more, preferably 95% or more, more preferably 98% or more and particularly preferably 100%) is preferably a hydrogen atom. Examples of protecting groups include a Z group, Boc group, acetyl group and trifluoroacetyl group normally used as protecting groups of amino groups.

$L^1$ and $L^2$ respectively and independently represent a linking group. Although there are no restrictions on the types of $L^1$ and $L^2$, a group represented by —$(CH_2)_b$—NH— (wherein, b represents an integer of 1 to 15) is preferable for $L^1$, while a group represented by —$(CH_2)_c$—CO— (wherein, c represents an integer of 1 to 15) is preferable for $L^2$.

m normally represents an integer of 5 or more, preferably 10 or more and more preferably 40 or more, and normally an integer of 20,000 or less, preferably 3,000 or less, more preferably 2,000 or less and particularly preferably 1,000 or less.

n normally represents an integer of 5 or more, preferably 10 or more and more preferably 40 or more, and normally an integer of 5,000 or less, preferably 1,000 or less, more preferably 500 or less and particularly preferably 300 or less.

x normally represents an integer of 0 or more, preferably 1 or more and more preferably 10 or more, and normally an integer of 5,000 or less, provided that x n.

y and z respectively and independently normally represent an integer of 0 or more and preferably 1 or more, and normally an integer of 5,000 or less, provided that y+z≤n, and particularly preferably 10≤y≤n−10 and 10≤z≤n−10.

Furthermore, in general formulae (I) to (IV), in the case the poly(amino acid or derivative thereof) segment has a plurality of types of repeating units, each repeating unit may form a block or may be randomly mixed.

In addition, in general formulae (I) to (IV), although a cationic group possessed by the poly(amino acid or derivative thereof) segment may be a free cationic group, it may also form a salt. In this case, although there are no particular restrictions on the counter ion that forms the salt, examples thereof include $Cl^-$, $Br^-$, $I^-$, $(\frac{1}{2}SO_4)^-$, $NO_3^-$, $(\frac{1}{2}CO_3)^-$, $(\frac{1}{3}PO_4)^-$, $CH_3COO^-$, $CF_3COO^-$, $CH_3SO_3^-$ and $CF_3SO_3^-$.

There are no particular limitations on the method used to produce the block copolymers represented by general formulae (I) to (IV), and examples thereof include the two types of methods explained below.

As an example of the first method, a PEG derivative having an amino group on the end thereof is used, a block copolymer is synthesized by polymerizing an N-carboxy anhydride (NCA) of a protecting amino acid such as β-benzyl-L-aspartate or NE-Z-lysine, and the protecting amino acid side chain of the subsequently resulting poly(amino acid derivative) segment is converted to a desired amino acid side chain. In this case, the structure of the resulting block copolymer is represented by general formula (I) or (III).

As an example of the second method, after synthesizing a poly(amino acid or derivative thereof) segment having a desired amino acid side chain, it is bonded to a PEG segment. In this case, the structure of the resulting block copolymer is represented by any of general formulae (I) to (IV).

Regardless of whether using the first method or the second method, in the case of subsequently introducing a desired amino acid side chain into the poly(amino acid or derivative thereof) segment, although the method used is arbitrary, in the case of a polyaspartic acid structure, for example, an example of that method is an exchange reaction in which an ester is converted to an amide by aminolysis of a poly(β-benzyl-L-aspartate) moiety as described in Japanese Patent No. 2777530. As an example of another method, after having hydrolyzed a benzyl ester by catalytic reduction, acid or base and the like to convert to polyaspartic acid or polyglutamic acid, compounds having these residues are bonded using a condensation agent.

In addition, in the case of using either the first method or the second method, in the case of subsequently introducing a protecting group, hydrophilic group or polymerizing group and the like onto the end of the block copolymer ($R^1$, $R^3$, $R^5$ or $R^6$), although the method used is arbitrary, an example of that method is a method used in ordinary synthesis, such as a method that uses an acid halide, a method that uses an acid anhydride or a method that uses an active ester.

[Cationic Polymer]

The cationic polymer is a polymer that has a cationic group and demonstrates cationic properties (positive ionic properties). However, the cationic polymer may also have some anionic groups within a range that does not impair the formation of polymer micelles.

There are no limitations on the type of cationic polymer. It may be a polymer composed of a single repeating unit, or may be a segment containing two or more types of repeating units in an arbitrary combination and ratio. The cationic polymer is preferably a polyamine, and particularly preferably a polyamino acid or derivative thereof having an amino group in a side chain thereof. Although examples of polyamino acids or derivatives thereof having an amino group in a side chain thereof include polyaspartamide, polyglutamide, polylysine, polyarginine, polyhistidine and derivatives thereof, polyaspartamide derivatives and polyglutamide derivatives are particularly preferable.

Although there are no limitations thereon, from the viewpoint of efficiently producing homogeneous polymer micelles, the molecular weight of the cationic polymer preferably has a molecular weight within a prescribed range. Although there are also no restrictions on the number of repeating units of the cationic polymer, normally the number of repeating units is determined corresponding to the types of repeating units so that the molecular weight of the cationic polymer satisfies the prescribed molecular weight range. More specifically, in the case of using a polyaspartic acid derivative or polyglutamic acid derivative for the cationic polymer, the number of repeating units thereof is within the range of preferably 5 or more and more preferably 10 or more to preferably 300 or less and more preferably 200 or less.

The use of a cationic polymer that satisfies the aforementioned conditions makes it possible to stabilize the block copolymer by preventing association and precipitation thereof in an aqueous solution, as well as efficiently form polymer micelles capable of functioning as a carrier composition.

(Specific Examples of Cationic Polymer)

Preferable specific examples of the cationic polymer of the present invention include poly(amino acids or derivatives thereof) represented by the following formulae (I') to (IV').

[Chemical Formula 8]

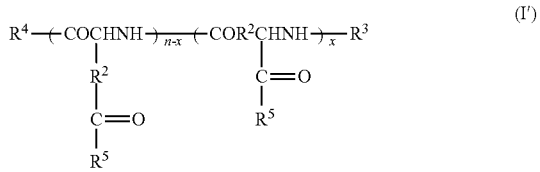

(I')

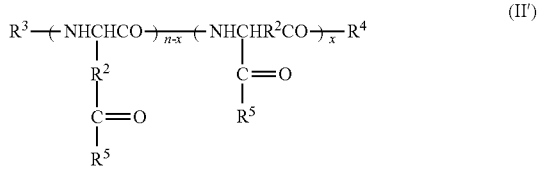

(II')

In formulae (I') and (II'), $R^2$, $R^3$, $R^4$, $R^5$, n and x are the same as groups having the same reference symbols previously defined in formulae (I) and (II)).

[Chemical Formula 9]

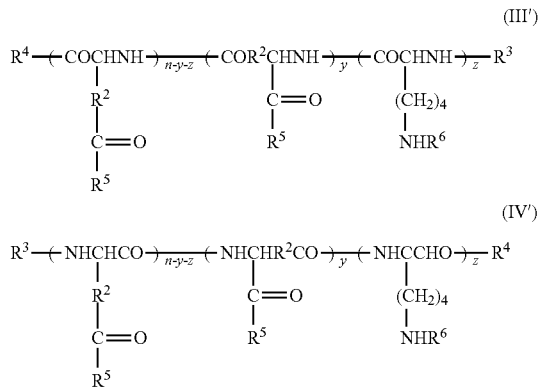

In formulae (III') and (IV'), $R^2$, $R^3$, $R^4$, $R^5$, $R^6$, n, x, y and z are the same as groups having the same reference symbols previously defined in formulae (III) and (IV).

Details regarding each of the groups in formulae (I') to (IV'), details regarding the poly(amino acids or derivative thereof) represented by formulae (I') to (IV'), and details regarding the production method thereof are as previously described regarding the poly(amino acid or derivative thereof) segment of the block copolymers represented by formulae (I) to (IV).

Furthermore, although X is normally selected from residues classified into the aforementioned group A to group E in the case $R^5$ in formulae (I') to (IV') represents an —NH—$(CH_2)_a$—X group, group B is preferable and the following amine compound residue is particularly preferable:

$$-(NR^7(CH_2)_d)_e-NH_2$$ [Chemical Formula 10]

In the formula, $R^7$ represents a hydrogen atom or methyl group, and d and e respectively and independently represent an integer of 1 to 5.

[B/H Ratio]

The ratio of the block copolymer and cationic polymer possessed by the nucleic acid delivery composition and carrier composition of the present invention is represented by the mol percentage of cationic groups possessed by the block copolymer to the total cationic groups possessed by the block copolymer and the cationic polymer (hereinafter also referred to as "B/H ratio"). More specifically, this ratio is represented by the equation indicated below.

$$\frac{B/H \text{ ratio}}{(\text{mol percentage})} = \frac{\text{Cationic groups of block copolymer}}{\text{Total cationic groups of block copolymer and cationic polymer}} \times 100(\%)$$ [Equation 1]

In the present invention, the aforementioned B/H ratio is normally within the range of more than 25%, preferably 30% or more, more preferably 40% or more and even more preferably 50% or more to normally 90% or less, preferably 85% or less and more preferably 80% or less. As a result of the B/H ratio being within the aforementioned range, a superior nucleic acid delivery composition can be obtained that is provided with both low cytotoxicity and high nucleic acid transfection efficiency.

In the present invention, although the reasons for being able to obtain such effects by making the B/H ratio to be within the aforementioned range are not clear, making the B/H ratio to be within a range equal to or greater than the aforementioned lower limit makes it possible to maintain the zeta potential at a value close to zero and adequately inhibit toxicity, while as a result of making the B/H ratio to be within a range equal to less than the aforementioned upper limit, particles can be maintained in a spherical or roughly spherical shape, particle stability can be enhanced in media and blood, and adequate nucleic acid transfection efficiency can be demonstrated, and this is presumed to result in the realization of both low cytotoxicity and high nucleic acid transfection efficiency.

Furthermore, in the case the nucleic acid delivery composition and carrier composition of the present invention contain two or more types of block copolymer and/or two or more types of cationic polymer, the overall B/H ratio of the two types of block copolymer and/or two or more types of cationic polymer satisfies the aforementioned range.

[Nucleic Acid]

There are no restrictions on the nucleic acid used in the nucleic acid delivery composition of the present invention. Namely, examples of nucleic acid include DNA, RNA, naturally-occurring or non-naturally-occurring nucleic acid analogues (such as peptide nucleic acids), altered nucleic acids and modified nucleic acids, and any of these may be used. In addition, the nucleic acid may be a single-stranded nucleic acid or double-stranded nucleic acid, and there are no restrictions on the presence or absence of a protein encoding function or other functions.

However, the nucleic acid is preferably a functional nucleic acid capable of demonstrating some form of action on the body, tissue or cells and the like in the case of being delivered to the body. Examples of functional nucleic acids include plasmid DNA, siRNA, miRNA (micro RNA), antisense RNA, antisense DNA, decoy nucleic acids, ribozymes, DNA enzymes, various types of suppressor genes (such as tumor suppressor genes), functionally altered nucleic acids and modified nucleic acids (such as nucleic acids in which the phosphoric acid moiety of the nucleic acid has been modified to a phosphorothioate, methyl phosphonate, phosphate triester or phosphoroamidate, or nucleic acids to which a hydrophobic functional group such as cholesterol or vitamin E has been bonded for use in applications such as polymer micelle stabilization). These nucleic acids are selected corresponding to the application of the nucleic acid delivery composition.

The plasmid DNA is that which is able to demonstrate a desired function in a target cell or tissue. Various types of plasmid DNA are known, and a desired plasmid DNA can be selected by a person with ordinary skill in the art corresponding to the application of the nucleic acid delivery composition.

In addition, the siRNA is that which is able to suppress the expression of a target gene using RNA interference (RNAi). Preferable examples of genes targeted for RNA interference include cancer (tumor) genes, anti-apoptotic genes, cell cycle-related genes and growth signal genes. In addition, although there are no limitations on the base length of the siRNA, it is normally less than 30 bases and preferably 19 to 21 bases.

Although one type of nucleic acid may be used, two or more types may also be used in an arbitrary combination and ratio.

Furthermore, since nucleic acid molecules are polyanions, they can be bonded (associated) with a side chain of the polycationic moiety of the aforementioned block copolymer by electrostatic interaction.

[N/P Ratio]

The ratio of nucleic acid to the block copolymer and cationic polymer is represented by the mol ratio of the [cationic groups of the block copolymer and the cationic polymer] to the [phosphate groups of the nucleic acid] (hereinafter referred to as "N/P ratio").

$$\frac{N/P \text{ ratio}}{(\text{mol ratio})} = \frac{\text{Cationic groups of block copolymer and cationic polymer}}{\text{phosphate groups of nucleic acid}} \quad \text{[Equation 2]}$$

In the present invention, although there are no limitations thereon, this N/P ratio is normally within the range of 2 or more, preferably 4 or more and more preferably 6 or more to normally 200 or less, preferably 100 or less and more preferably 50 or less. Since the nucleic acid delivery composition of the present invention has superior nucleic acid transfection efficiency in comparison with conventional PIC polymer micelle-type nucleic acid delivery compositions, nucleic acid can be efficiently delivered and genes can be expressed using a smaller amount of nucleic acid than the conventionally used amount (namely, at a lower N/P ratio than in the past).

[Other Components]

When producing the nucleic acid delivery composition and carrier composition of the present invention, other components can be added in addition to the block copolymer cationic polymer and nucleic acid within a range that does not impair the formation of polymer micelles and does not lower their stability. Although there are no particular limitations thereon, specific examples of other components include uncharged or charged polymers and charged nanoparticles.

Examples of uncharged or charged polymers include any uncharged or charged polymers other than the block copolymer and cationic polymer previously described.

Examples of charged nanoparticles include metal nanoparticles having a charge on the surface thereof.

One type of the aforementioned other components may be used alone, or two or more types may be combined in an arbitrary combination and ratio.

Although there are no restrictions on the amount of other components used, it is preferably an amount that does not impair the formation of polymer micelles. More specifically, the amount of other components used is normally 30% or less, preferably 20% or less and more preferably 10% or less based on the total weight of the composition of the present invention.

[Preparation Method of Carrier Composition]

The carrier composition of the present invention is prepared by mixing the aforementioned block copolymer, cationic polymer and other components used as necessary.

More specifically, a first aqueous solution containing the block copolymer, and a second aqueous solution containing the cationic polymer are prepared. The first and second aqueous solutions may be purified by filtering as desired.

There are no limitations on the concentration of block copolymer in the first aqueous solution or the concentration of cationic polymer in the second aqueous solution, and are suitably determined in consideration of conditions such as the ratio of the block copolymer and cationic polymer, the solubility of the block copolymer and cationic polymer in aqueous solution, or the formation efficiency of the polymer micelles.

There are no limitations on the type of solvent of the first and second aqueous solutions provided it is an aqueous solvent. Although water is preferable, a solvent obtained by mixing other components with water can also be used within a range that does not impair the formation of polymer micelles, examples of which include physiological saline, aqueous buffers and mixed solvents of water and a water-soluble organic solvent. An example of an aqueous buffer is 10 mM HEPES buffer.

Although the pH of the first and second aqueous solutions can be suitably adjusted to a range that does not impair the formation of polymer micelles, it is preferably within the range of 5 or higher or more preferably 6.5 or higher to preferably 9 or lower and more preferably 7.5 or lower. The pH can be easily adjusted by using a buffer for the solvent. Using the first and second aqueous solutions after adjusting the pH thereof is advantageous in terms of maintaining the charged states of the block copolymer and cationic polymer and efficiently forming polymer micelles.

Although the salt concentration of the first and second aqueous solutions can be suitably adjusted to a range that does not impair the formation of polymer micelles, it is preferably within the range of 5 mM or more or more preferably 10 mM or more to preferably 300 mM or less and more preferably 150 mM or less.

There are no limitations on the method used to mix the first and second aqueous solutions. The second aqueous solution may be added to the first aqueous solution or the first aqueous solution may be added to the second aqueous solution. In addition, the first and second aqueous solutions may be simultaneously added to a container and mixed. The resulting mixture of the first and second aqueous solutions may then be suitably stirred.

Although there are no limitations on the temperature when mixing the first and second aqueous solutions provided it is within a range that does not impair the formation of polymer micelles, it is preferably set in consideration of the solubilities of the block copolymer and cationic polymer corresponding to temperature. More specifically, the temperature is normally 0° C. or higher and preferably 60° C. or lower, and more preferably 50° C. or lower.

After mixing, although the carrier composition containing the formed polymer micelles may be used directly in a desired application, the mixture may be allowed to stand undisturbed for a time in order to equilibrate the system. Although the amount of the time the mixture is allowed to stand undisturbed varies according to conditions such as the formation efficiency of the polymer micelles, it is preferably 50 hours or less and more preferably 30 hours or less. However, in the case of not using a crosslinking agent as previously described, since the diameter of the formed polymer micelles tends to increase over time, there are cases in which it is not preferable to allow the mixture to stand undisturbed.

In the case of using other components in addition to the block copolymer and cationic polymer, the other components are added and mixed during or after mixing the aforementioned first and second aqueous solutions. Although the other components may be added and mixed directly, they may also be mixed after having prepared an aqueous solution containing the other components. Preparation conditions such as the aqueous solvent, pH, temperature or ionic strength during preparation of an aqueous solution of the other components are the same as the conditions previously described for the first and second aqueous solutions.

In addition, a procedure such as dialysis, dilution, concentration or stirring may be further suitably added.

[Preparation Method of Nucleic Acid Delivery Composition]

The nucleic acid delivery composition of the present invention is normally prepared by (i) mixing the aforementioned nucleic acid with the aforementioned block copolymer, cationic polymer and other components used as necessary, or by (ii) mixing the aforementioned nucleic acid with the preliminarily prepared carrier composition of the present invention.

In the case of (i), a nucleic acid may be further added and mixed when mixing the aforementioned first aqueous solution (aqueous solution of the block copolymer) and second aqueous solution (aqueous solution of the cationic polymer) in the aforementioned preparation procedure of the carrier composition. In addition, the first aqueous solution and the second aqueous solution may be mixed after having preliminarily added and mixed a nucleic acid with the first aqueous solution or the second aqueous solution.

In the case of (ii), a nucleic acid is further added and mixed with the carrier composition obtained by mixing the aforementioned first aqueous solution (aqueous solution of the block copolymer) and second aqueous solution (aqueous solution of the cationic polymer). Although the nucleic acid may be added and mixed immediately after preparing the carrier composition by mixing the first and second aqueous solutions, the nucleic acid may be further added and mixed after allowing the system to equilibrate by allowing the mixture to stand undisturbed.

In either the case of (i) or (ii), although the nucleic acid may be added and mixed directly, an aqueous solution containing the nucleic acid (third aqueous solution) may be prepared followed by adding and mixing that aqueous solution. Preparation conditions such as the aqueous solvent, pH, temperature or ionic strength during preparation of the third aqueous solution are the same as the conditions previously described for the first and second aqueous solutions.

In addition, a procedure such as dialysis, dilution, concentration or stirring may be further suitably added.

[Structures of Nucleic Acid Delivery Composition and Carrier Composition]

Although there are no limitations thereon, the shape of the nucleic acid delivery composition and carrier composition of the present invention is normally spherical or roughly spherical.

Although varying according to the type and weight ratio of the block copolymer and cationic polymer, the presence or absence of other components, the surrounding environment of the nucleic acid delivery composition and the carrier composition (such as the type of aqueous medium) and the like, the particle diameter of the nucleic acid delivery composition and carrier composition of the present invention is preferably 10 nm or more and more preferably 50 nm or more, and preferably 200 nm or less and more preferably 150 nm or less.

Furthermore, although the particle diameter of the nucleic acid delivery composition and carrier composition tends to increase over time under conditions in which a salt is present such as in a physiological environment or physiological saline, increases in particle diameter can be prevented by introducing a crosslinking agent.

Although the particle internal structure of the nucleic acid delivery composition and carrier composition of the present invention is uncertain, it is surmised to be as described below when considering that the zeta potential is close to 0 as will be subsequently described.

In the carrier composition, the particles are thought to have the structure of PIC polymer micelles in which the hydrophilic segment of the block copolymer is densely present around the periphery of the particle outer shell, while the cationic polymer segment of the block copolymer and the cationic polymer are mainly present inside the particles.

In addition, in the nucleic acid delivery composition as well, the particles are also thought to have the structure of PIC polymer micelles in which, although the hydrophilic segment of the block copolymer is similarly densely present around the periphery of the particle outer shell, the cationic polymer segment of the block copolymer and the cationic polymer are electrostatically coupled to a nucleic acid and are mainly present in a state of being included and supported inside the particles.

[Applications of Nucleic Acid Delivery Composition and Carrier Composition]

The nucleic acid delivery composition of the present invention can be used to deliver a nucleic acid(s) to a target cell(s) or tissue(s) either in vitro or in vivo.

According to the nucleic acid delivery composition of the present invention, in addition to being able to deliver nucleic acids in stable complexes easily, for which efficient delivery to target cells was difficult due to the instability of the complex, cytotoxicity can be suppressed. In addition, the nucleic acid delivery composition of the present invention can also be used as means for efficiently introducing nucleic acids encapsulated and held within particles of the nucleic acid delivery composition into target cells by utilizing a difference in pH of intracellular compartment and extracellular environment. Moreover, in the case of using a nucleic acid encoding gene(s) of protein(s) aiming to be able to express the gene(s) in cells or tissue, high gene expression efficiency can be obtained by using the nucleic acid delivery composition of the present invention.

The nucleic acid delivery composition of the present invention is in a state that is able to contact a target cell or tissue in order to deliver a nucleic acid to the target cell or tissue using the nucleic acid delivery composition.

In order to achieve contact between the nucleic acid delivery composition of the present invention and a target cell or tissue in vitro, the target cell or tissue is cultured in the presence of the nucleic acid delivery composition of the present invention, or the nucleic acid delivery composition is added to a culture of the target cell or tissue.

In order to achieve contact between the nucleic acid delivery composition of the present invention and a target cell or tissue in vivo, the nucleic acid delivery composition of the present invention is administered to an individual (individual to be treated) requiring introduction of the nucleic acid by an administration method commonly used in the relevant technical field such as gene therapy. There are no limitations on such an individual, and examples thereof include humans, mice, rats, rabbits, dogs, cats, monkeys, cows, horses, pigs and birds. Examples of administration methods include direct transfection to the vicinity of or inside a target cell or tissue or transplantation, intravenous injection, intraarterial injection, intramuscular injection, oral administration and transpulmonary administration. Various conditions such as dosage, number of administrations or administration period can be suitably set according to the type, status and so forth of the test animal.

Furthermore, since the lung in particularly is highly sensitive to extrinsic foreign bodies, there are cases in which inflammation may be induced in the case of drug delivery using a conventional DDS, and although transpulmonary administration is extremely difficult for this reason, according to the nucleic acid delivery composition of the present invention, since toxicity can be suppressed to a low level and high gene expression efficiency can be obtained, it can also be used preferably for transpulmonary administration.

In addition, the carrier composition of the present invention can be used in applications similar to those of the aforementioned nucleic acid delivery composition by encapsulating a nucleic acid to realize the nucleic acid delivery composition of the present invention. The method used to encapsulate the nucleic acid is as was described in the section entitled "Preparation Method of Nucleic Acid Delivery Composition".

[Pharmaceutical Composition]

According to the present invention, a pharmaceutical composition can also be provided that comprises the nucleic acid delivery composition or carrier composition of the present invention (pharmaceutical composition of the present invention). The pharmaceutical composition of the present invention can be used, for example, in therapy consisting of delivering and introducing desired nucleic acids that targets cells or tissue causing various types of diseases (gene therapy).

Individuals able to be administered with the pharmaceutical composition of the present invention are the same as those previously described for the nucleic acid delivery composition. Although there are no restrictions thereon, examples of diseases targeted for therapy using the pharmaceutical composition of the present invention include cancer (such as lung cancer, pancreatic cancer, brain tumor, liver cancer, breast cancer, colorectal cancer, neuroblastoma or bladder cancer), cerebrovascular disease, motor disorders and central nervous system diseases.

The pharmaceutical composition of the present invention may also contain other components typically used in pharmaceutical production in addition to the nucleic acid delivery composition or carrier composition of the present invention. Examples of other components include vehicles, extenders, fillers, binders, wetting agents, disintegration agents, lubricants, surfactants, dispersants, buffers, preservatives, solubilizing agents, antiseptics, correctives, soothing agents, stabilizers and tonicity agents. One type of these other components may be used alone or two or more types may be used in an arbitrary combination and ratio. Details of these other components, such as the type of component and amount used, can be suitably determined by a person with ordinary skill in the art corresponding to the purpose, application, usage method and so forth of the pharmaceutical composition.

Although the form of the pharmaceutical composition of the present invention is arbitrary, it is normally used in the form of an intravenous injection preparation (including intravenous infusion), and is supplied in the form of, for example, single-dose ampules or multi-dose containers.

The usage method of the pharmaceutical composition of the present invention is also arbitrary. A pharmaceutical composition containing the nucleic acid delivery composition can be administered directly. In the case of a pharmaceutical composition containing a carrier composition but not containing a nucleic acid, the pharmaceutical composition is administered after mixing the nucleic acid with the carrier composition to be encapsulated prior to use.

[Nucleic Acid Delivery Method]

In addition, according to the present invention, a method is provided for delivering a nucleic acid(s) to a target cell(s) or tissue(s) in vitro or in vivo (nucleic acid delivery method of the present invention). The nucleic acid delivery method of the present invention includes the following methods (1) and (2).

(1) Method Using Nucleic Acid Delivery Composition or Pharmaceutical Composition of Present Invention In this method, nucleic acids are delivered to target cells or tissue by using the previously explained nucleic acid delivery composition or pharmaceutical composition of the present invention, and contacting those with the target cells or tissue in vitro or in vivo. The details of the nucleic acid delivery composition and pharmaceutical composition, and the method used to contact the target cell or tissue and the like are as previously described. According to this method, cytotoxicity can be suppressed to a low level and the nucleic acid can be transfected with high efficiency in the same manner as was previously described.

(2) Method of Combining Composition Containing Block Copolymer and Nucleic Acid with Cationic Polymer in Situ In this method, a composition obtained by excluding the cationic polymer from the nucleic acid delivery composition or pharmaceutical composition of the present invention (namely, a composition containing the block copolymer and nucleic acid, and to be referred to as a block copolymer-based nucleic acid composition in the subsequent description) is used, and contacted with target cells or tissue in vitro or in vivo separately with cationic polymer, those are combined in situ. Moreover, the ratio at which the block copolymer of the block copolymer-based nucleic acid composition and the cationic polymer are present in the target cell or tissue is adjusted to a ratio so that the B/H ratio satisfies the aforementioned specific range. According to this method (2) as well, cytotoxicity can be suppressed to a low level and the nucleic acid can be transfected with high efficiency in the same manner as the aforementioned method (1) (method for delivering nucleic acid using the nucleic acid delivery composition of the present invention).

The details of the method (2) are as described below.

Details of the block copolymer and nucleic acid that compose the block copolymer-based nucleic acid composition are as previously described regarding the nucleic acid delivery composition of the present invention. The ratio at which the block copolymer and nucleic acid are used is arbitrary, and although it may be suitably selected corresponding to the purpose, conditions and so forth of nucleic acid delivery, in consideration of the ratio at which the cationic polymer is combined in situ, a ratio is preferably used so that the aforementioned N/P ratio is satisfied. The block copolymer-based nucleic acid composition can also be prepared by mixing each component in compliance with preparation of the nucleic acid delivery composition of the present invention.

Details regarding the cationic polymer are also as previously described regarding the nucleic acid delivery composition of the present invention.

The previously described method for contacting the nucleic acid delivery composition of the present invention with a target cell or tissue can be used for the method used to contact the block copolymer-based nucleic acid composition and cationic polymer with target cells or tissue. However, in order to achieve the desired N/P ratio in situ, a method is preferably used that enables each concentration of the block copolymer-based nucleic acid composition and cationic polymer to be accurately controlled to a certain degree in situ. Examples of preferable contact methods for achieving this control of concentration in vitro include a method consisting of preliminarily adding to the medium prior to culture, and a method consisting of subsequently adding to a medium or culturing material during culture. In addition, examples of preferable contact methods for achieving this control of concentration in vivo include local administration and intravascular administration. Furthermore, administration is preferably in a form mixed with a commonly known anionic polymer in order to increase contact efficiency with cells or tissue of the cationic polymer in particular.

Furthermore, there are no limitations on the order in which the block copolymer-based nucleic acid composition and cationic polymer are contacted with the target cells or tissue, and they may be contacted in an arbitrary order. Namely, although the block copolymer-based nucleic acid composition and cationic polymer may be contacted with the target cell or tissue simultaneously, either may be first contacted with the target cells or tissue followed by contacting the other with the target cells or tissue. In the case of contacting both with the target cells or tissue simultaneously, both may be separately contacted with the target cells or tissue or both may be contacted with the target cells or tissue after mixing. In the case of separately contacting with the target cells or tissue, the contact methods used may be the same or different.

Although the nucleic acid delivery method of the present invention can be used in various applications, it can be used particularly preferably in therapy consisting of delivering and introducing desired nucleic acids that targets cells or tissue causing various types of diseases (gene therapy).

EXAMPLES

The following provides a more detailed explanation of the present invention while referring to examples thereof. Furthermore, the following examples are intended to merely be exemplary and do not limit the present invention in any way.

Example Group I

Study of Physical Properties and In Vitro Characteristics of Nucleic Acid Delivery Composition (Block Copolymer)
<Structure of PEG-PAsp(DET)>

A block copolymer indicated below having a polyethylene glycol (hereinafter also referred to as "PEG") segment and a poly(aspartic acid-diethylenetriamine derivative) (hereinafter also referred to as "PAsp(DET)") segment was used for the block copolymer (hereinafter also referred to as "PEG-PAsp (DET)"):

In the above formula, m indicates the degree of polymerization of PEG and is approximately 270, n indicates the degree of polymerization of PAsp(DET) and is approximately 61, a and b represent a number that is greater than 0 and less than 1, provided that a+b=1, and c indicates the number of repeating units of the ethylene group serving as a linking group and is approximately 3).

The molecular weight of the PEG segment of PEG-PAsp (DET) was approximately 12000, and the molecular weight of the PAsp(DET) segment was approximately 14000.

<Production Method of PEG-PAsp(DET)>

PEG-PAsp(DET) was produced according to the following procedures (1) and (2).

(1) Synthesis of PEG-polybenzyl-L-aspartate (PEG-PBLA)

An amino acid N-carboxy anhydride (NCA) compound was dissolved in a small amount of dimethylformamide (DMF) followed by the addition of methylene chloride thereto. PEG having a primary amino group on one end and dissolved in dichloromethane was added as polymerization initiator and stirred for 2 days at 35° C. was used a polymerization initiator. This procedure was carried out in a dry argon atmosphere. The PEG-PBLA formed was precipitated by dropping into a mixed solvent of n-hexane and ethyl acetate (6/4), recovered by filtering, and then drying under reduced pressure. When the molecular weight distribution of the PEG-PBLA formed was analyzed by gel filtration chromatography (GPC) using a calibration curve prepared with PEG standards, the ratio of weight average molecular weight (Mw) to number average molecular weight (Mn) was 1.05. In addition, the degree of polymerization was determined to be 65 by $^1$H NMR measurement.

(2) Synthesis of PEG-PAsp(DET)

PEG-PAsp(DET) was synthesized using an aminolysis reaction of PEG-PBLA. 50 mg of dried PEG-PBLA were dissolved in 2 mL of N-methylpyrrolidone (NMP) and cooled to 5° C. A solution in which DET in an amount equal to 50 times the number of moles of benzylester groups of PEG-PBLA was diluted with NMP was prepared in a separate vessel and cooled to the same temperature as the aforementioned PEG-PBLA solution. The aforementioned PEG-PBLA solution was slowly dropped therein, and after allowing to react for 1 hour, the reaction solution was dropped into chilled 5 N HCl (preferably a dilute acid of about 1 N) while

[Chemical Formula 11]

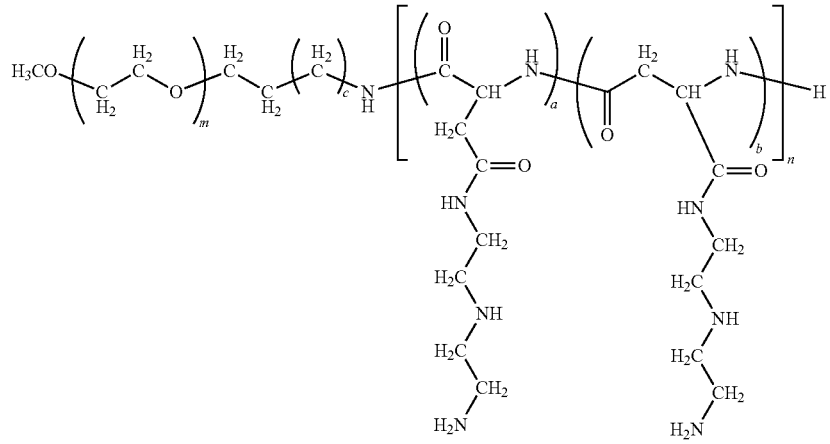

controlling the solution temperature to 5° C. or lower. Subsequently, dialysis was carried out while holding at 4° C. against an aqueous HCl solution of about 0.01 N (pH 2) followed by dialyzing against pure water to remove the excess acid. The finally obtained aqueous polymer solution was then freeze-dried and PEG-PAsp(DET) was recovered in the form of a salt. The aminolysis reaction was confirmed to be quantitative by $^1$H NMR measurement.

(Cationic Polymer)
<Structure of Homo-PAsp(DET)>

A poly(aspartic acid-diethylenetriamine derivative) homopolymer indicated below (hereinafter also referred to as "Homo-PAsp(DET)") was used for the cationic polymer.

[Chemical Formula 12]

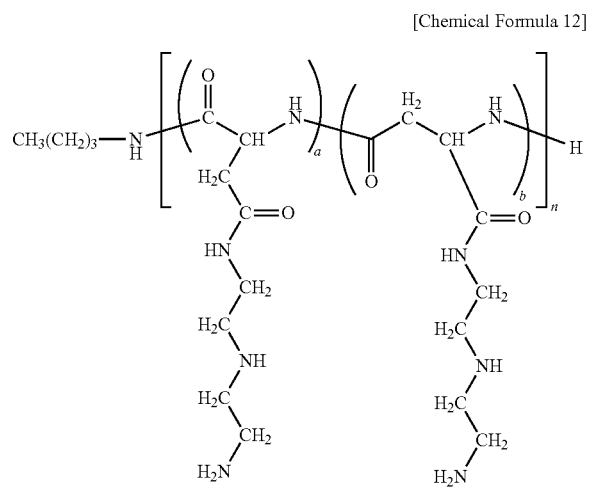

In the above formula, n indicates the degree of polymerization of PAsp(DET) and is approximately 54, and a and b represent a number that is greater than 0 and less than 1, provided that a+b=1).

Furthermore, the molecular weight of the aforementioned Homo-PAsp(DET) was approximately 10000.

<Production Method of Homo-PAsp(DET)>

Homo-PAsp(DET) was produced in compliance with the aforementioned <Production Method of PEG-PAsp(DET)>.

Namely, polybenzyl-L-aspartate (PBLA) was prepared by carrying out the same procedure as step (1) of the aforementioned <Production Method of PEG-PAsp(DET)> with the exception of using n-butylamine instead of PEG. Mw/Mn as determined by GPC was 1.06 and degree of polymerization as determined by $^1$H NMR measurement was 65.

Next, Homo-PAsp(DET) was prepared by carrying out the same procedure as step (1) of the aforementioned <Production Method of PEG-PAsp(DET)> with the exception of using 50 mg of the PBLA obtained above instead of PEG-PBLA.

(Nucleic Acid)

A plasmid encoding luciferase (Luc pDNA) was used for the nucleic acid. This plasmid was acquired from the Riken Cell Bank, introduced into *Escherichia coli*, amplified by culturing and used after purifying using NucleoBond® Xtra Maxi (Nippon Genetics Co., Ltd.).

(Preparation of Nucleic Acid Delivery Composition)

A composition (nucleic acid delivery composition) was prepared according to the following procedure using the aforementioned block copolymer (PEG-PAsp(DET)), cationic polymer (Homo-PAsp(DET)) and nucleic acid (Luc pDNA). Furthermore, in the case the term "solution" is simply indicated in subsequent descriptions, it refers to a 10 mM HEPES buffer solution.

After mixing 1 mg/mL block copolymer solution and 1 mg/mL cationic polymer solution so that the B/H ratio satisfies the various values to be subsequently described, the mixture was mixed with a prescribed amount of the pDNA in 10 mM HEPES buffer so that the N/P value satisfies the various values to be subsequently described to obtain a composition (nucleic acid delivery composition).

(Observation of Particle Shape)

Compositions (nucleic acid delivery compositions) were used that had been prepared using the aforementioned procedure in which the B/H ratio was made to be 100% (block copolymer alone), 75%, 50%, 25% or 0% (cationic polymer alone), and the N/P ratio was made to be 3. After staining nucleic acid in each of the compositions (nucleic acid delivery compositions) using an aqueous uranyl acetate solution, the shape of the particles was observed with a transmission electron microscope.

Transmission electron micrographs obtained for each of the compositions are shown in FIG. 1(a) and FIG. 1(b). Each of the micrographs of FIG. 1(b) is an enlarged micrograph of typical particles present in the corresponding micrograph of FIG. 1(a). In contrast to particle diameter being comparatively large in the 100% composition and the particle shape being comparatively long and narrow, particle diameter can be seen to gradually decrease and particle shape can be seen to become more spherical as the B/H ratio decreases.

(Measurement of Zeta Potential)

Compositions (nucleic acid delivery compositions) were used that had been prepared using the aforementioned procedure in which the B/H ratio was made to be 100% (block copolymer alone), 75%, 50%, 25% or 0% (cationic polymer alone), and the N/P ratio was made to be 3. The zeta potential of each composition (nucleic acid delivery composition) was measured according to the procedure described below.

Each composition was injected into a folded capillary cell (Malvern Instruments, Ltd.) and measured using Nano ZS (Malvern Instruments, Ltd.). Zeta potential was then calculated from the results obtained using the Smoluchowski equation as indicated below:

$$\zeta = 4\pi\eta\upsilon/e \qquad \text{Smoluchowski equation}$$

where $\zeta$ represents the zeta potential, $\eta$ represents the viscosity of the solvent, $\upsilon$ represents electrophoretic mobility, and e represents the dielectric constant of the solvent.

Figure 2:
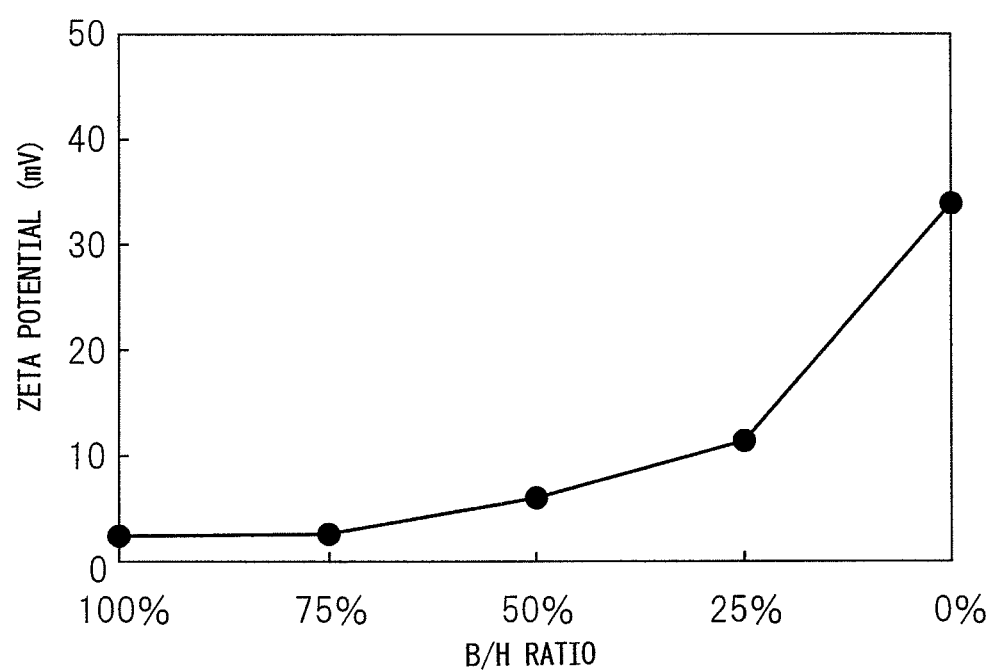
FIG. 2 is a graph showing the relationship between B/H ratio and zeta potential.

The relationship between the resulting zeta potential and B/H ratio values is indicated by the graph of FIG. 2. In contrast to the zeta potential being close to 0 mV within a range of B/H ratios of 25% or more, zeta potential increased suddenly when the B/H ratio decreased to below 25%. It is presumed on the basis thereof that, when the B/H ratio is within the range of 25% or more, PIC polymer micelles are presumed to be formed in which the uncharged hydrophilic polymer segment of the block copolymer is present on the outside of the particles, while the cationic polymer segment of the block copolymer is electrostatically coupled to the nucleic acid and present inside the particles.

(Measurement of Transfection Efficiency and Cytotoxicity)

Compositions (nucleic acid delivery compositions) were used that had been prepared using the aforementioned procedure in which the B/H ratio was made to be 100% (block copolymer alone), 80%, 70%, 60%, 50%, 25% or 0% (cationic polymer alone), and the N/P ratio was made to be 4, 6, 8, 12 or 16. The transfection efficiency and cytotoxicity of each composition (nucleic acid delivery composition) were measured according to the procedure indicated below.

Normal human umbilical vein endothelial cells (HUVEC) were disseminated with 400 μL of EBM-2 in a 24-well plate to a cell density of 20,000 cells per well followed by culturing for 24 hours. Subsequently, 30 μl aliquots of each composition (nucleic acid delivery composition) were added to each well followed by additionally culturing for 24 hours. The cells were washed with PBS followed by the addition of 400 μL aliquots of fresh EBM-2 to each well and further culturing for 24 hours. Subsequently, the number of viable cells in each well was counted using a cell counting kit (Cell Counting Kit-8: Chemical-Dojin Co., Ltd.) in accordance with the instruction manual and used as an indicator of cytotoxicity.

Continuing, the medium was removed and the cells were gently washed with PBS. 200 μL aliquots of cell lysis solution (Cell Culture Lysis Buffer: Promega Corp.) were added to each well, and luciferase activity was determined by measuring photoluminescence intensity using a luciferase assay kit (Luciferase Assay System Kit: Promega Corp.) and an LB940 reader (Mithras Corp.) and used as an indicator of transfection efficiency. Furthermore, the amount of protein in the cell lysis solution was determined using the MicroBCA® Protein Assay Reagent Kit (Thermo Scientific Inc.).

Figure 3:
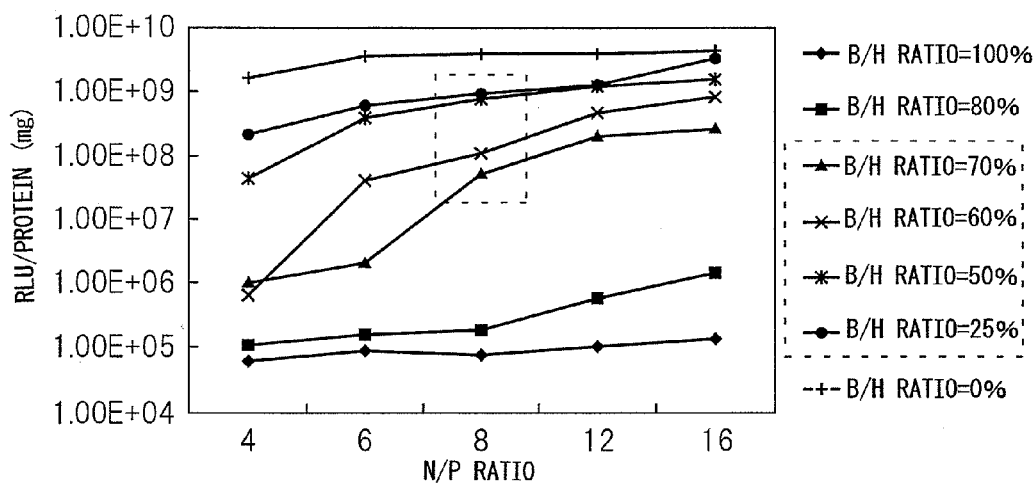
FIG. 3 is a graph showing the relationship between transfection efficiency and either B/H ratio or N/P ratio.

A graph indicating the relationship between transfection efficiency, B/H ratio and N/P ratio obtained for each of the compositions (nucleic acid delivery compositions) is shown in FIG. 3. In contrast to the composition having a B/H ratio of 100% demonstrating extremely low transfection efficiency, a definite improvement in transfection efficiency was observed for those compositions having a B/H ratio of 80% or more. In addition, an improvement in transfection ratio was also observed as N/P ratio increased regardless of the B/H ratio.

Figure 4:
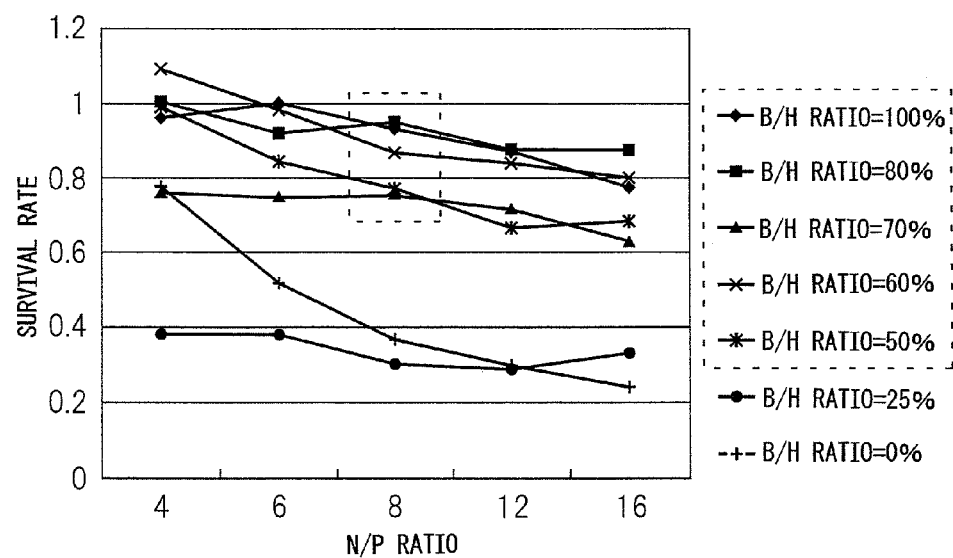
FIG. 4 is a graph showing the relationship between cytotoxicity and either B/H ratio or N/P ratio.

In addition, the relationship between cytotoxicity, B/H ratio and N/P ratio obtained for each of the compositions (nucleic acid delivery compositions) is shown in FIG. 4. In contrast to those compositions having a B/H ration of 25% or less having an extremely low number of viable cells and exhibiting comparatively high cytotoxicity, in those compositions having a B/H ratio of greater than 25%, the number of viable cells increased and a definite decrease in cytotoxicity was observed. In addition, decreases in cytotoxicity were also observed as N/P ratio increased regardless of the B/H ratio (decreases in cytotoxicity were also observed as N/P ratio decreased at a fixed B/H ratio).

Example Group II

Study of In Vivo Characteristics of Nucleic Acid Delivery Composition (Block Copolymer)

A block copolymer for which c=3 or c=6 in the PEG-PAsp (DET) represented by the formula of Example Group I was used for the block copolymer (hereinafter also referred to as "PEG-C3-PAsp(DET)" and "PEG-C6-PAsp(DET)", respectively, and also indicated as "C3" and "C6", respectively, in FIG. 5). Each polymer was synthesized in compliance with the method described in <Production Method of PEG-PAsp (DET)> of Example Group I.

(Cationic Polymer)

The same Homo-PAsp(DET) as that used in Example Group I was used for the cationic polymer.

(Nucleic Acid)

Any of the following nucleic acids were used.

*Plasmid Encoding sFlt-1 (sFlt-1 pDNA)

sFlt-1 refers to human sFlt-1 cDNA (2.4 kb) excised from pVL1393 papillovirus vector (pDNA) that was provided by Professor Shibuya of the Tokyo Medical and Dental University. After purifying by agarose gel electrophoresis, the pDNA was inserted into a pCAcc vector using the Rapid DNA Ligation Kit (Roche Diagnostics GmbH) and amplified by culturing in *Escherichia coli* (DH5α), about 10 colonies each that formed on the culture plates were picked from the plates and further cultured, each pDNA was examined by agarose gel electrophoresis and the like to select pDNA into which a desired sequence had been inserted, and the amplified product thereof was used after purifying using NucleoBond® Xtra (Nippon Genetics Co., Ltd.).

*Plasmid Encoding Fluorescent Protein (Venus) (Venus pDNA)

Venus pDNA was acquired from the Riken Cell Bank, amplified by culturing after introducing into *Escherichia coli*, and used after purifying using NucleoBond® Xtra Maxi (Nippon Genetics Co., Ltd.).

*Plasmid Encoding Luciferase (Luc pDNA)

This plasmid was acquired and prepared in the same manner as Example Group I.

*Cy5-Labeled Plasmid Encoding Luciferase (Cy5-pDNA)

This plasmid was obtained by labeling the aforementioned Luc pDNA with Cy5. Cy5 was labeled using the Label IT Nucleic Acid Labeling Kit purchased from Mirus Bio Corp. in accordance with the procedure described in the instruction manual.

(Animals)

8-week-old Balb/c mice (females, acquired from Charles River Laboratories Japan Inc.) were used as is, or 5-week-old nude Balb/c mice (females, acquired from Charles River Laboratories Japan Inc.) were used following subcutaneous inoculation with human pancreatic cancer BxPC3 cells and housing for 2 to 3 weeks until tumor volume grew to about 45 mm$^3$ (hereinafter also referred to as "BxPC3 subcutaneously inoculated mice").

(Preparation Method)

Compositions (nucleic acid delivery compositions) were prepared using the aforementioned block copolymers (PEG-C3-PAsp(DET) or PEG-C6-PAsp(DET)), cationic polymer (Homo-PAsp(DET)) and nucleic acids (sFlt-1 pDNA, Cy5-pDNA, Venus pDNA or Luc pDNA) in accordance with the procedure described in (Preparation of Nucleic Acid Delivery Composition) of Example Group 1 while changing the B/H ratio to the various values described for each of the following parameters and making the N/P ratio 8.

(Measurement of Time-Based Changes in Tumor Volume by Intravenous Infusion)

Compositions (nucleic acid delivery compositions) (2OD, 200 μL) obtained using PEG-C3-PAsp(DET) or PEG-C6-PAsp(DET) for the block copolymer, using sFlt-1 pDNA for the nucleic acid, and making the B/H ratio 100% (block copolymer alone), 70% or 50% were each administered systemically by intravenous infusion to the aforementioned BxPC3 subcutaneously inoculated mice (using 6 animals per composition). Each animal was administered with the compositions on day 0, day 4 and day 8 after the start of the experiment. The dosage used for each administration was determined so that the dosage of nucleic acid per mouse was 20 μg. Tumor suppressor effects induced by nucleic acid delivery were examined by measuring tumor volume over time following the start of the experiment.

In addition, a control experiment was also carried out by administering the compositions and measuring tumor volume in the same manner as described above using 10 mM HEPES buffer.

Figure 5:
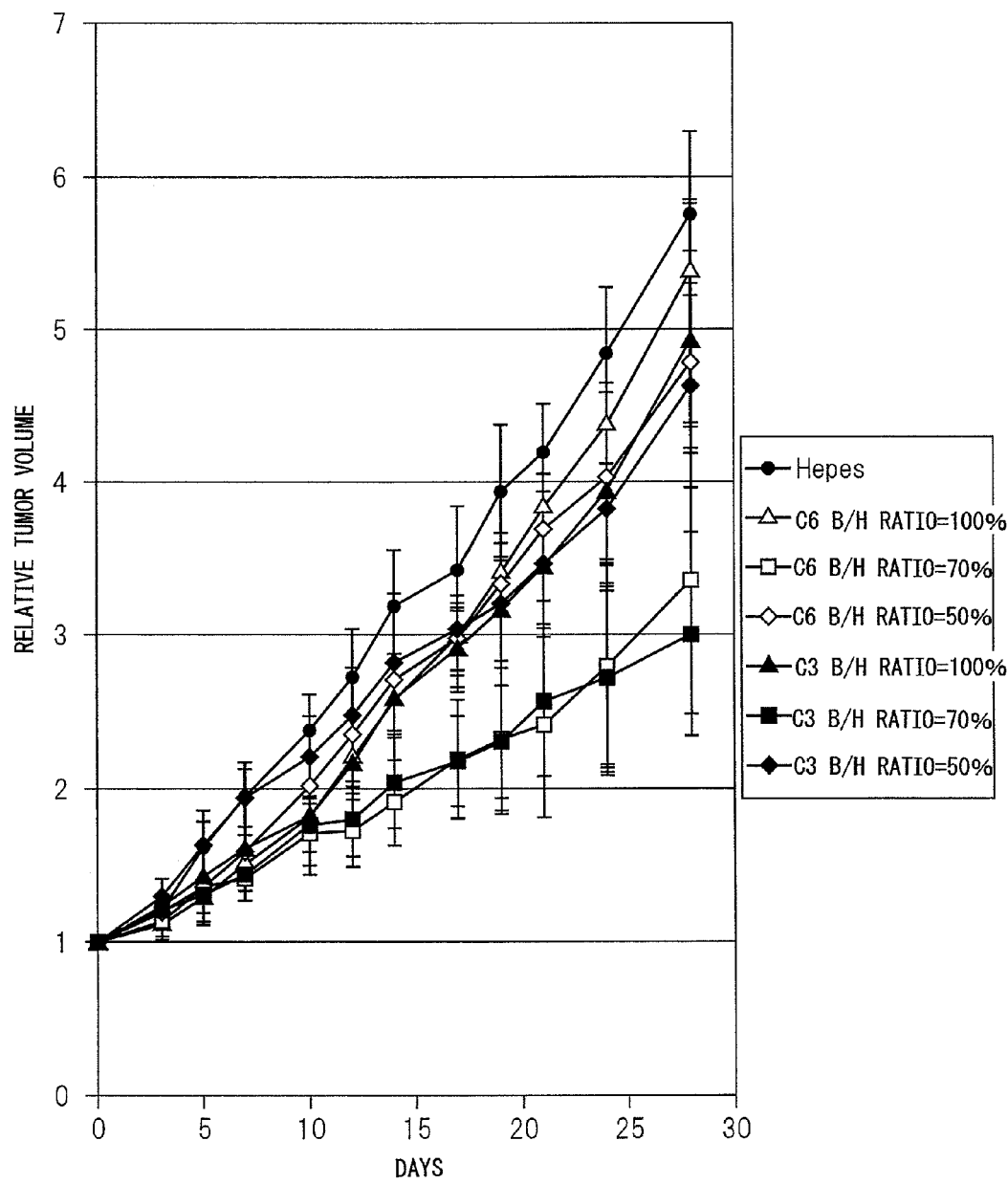
FIG. 5 is a graph showing change in tumor volume over time.

A graph indicating the time-based changes in tumor volume obtained for each B/H ratio is shown in FIG. 5. In the case of using either PEG-C3-PAsp(DET) (indicated as "C3" in FIG. 5) or PEG-C6-PAsp(DET) (indicated as "C6" in FIG. 5), tumor suppressor effects were observed to a greater degree in comparison with the case of the control (HEPES buffer). These effects were more prominent for the compositions having a B/H ratio of 50% or 70% in comparison with the composition having a B/H ratio of 100%, and particularly remarkable tumor suppressor effects were observed for the composition having a B/H ratio of 70%.

(Measurement of Blood Retention of Nucleic Acid Delivery Composition by Intravenous Infusion)

Compositions (nucleic acid delivery compositions) (2OD, 200 µL) obtained using PEG-C3-PAsp(DET) for the block copolymer, using Cy5-pDNA for the nucleic acid, and making the B/H ratio 100% (block copolymer alone), 70% or 50% were each administered systemically by intravenous infusion to the aforementioned BxPC3 subcutaneously inoculated mice (using 8 animals per composition). The dosage was determined so that the dosage of nucleic acid per mouse was 20 µg. Blood samples were collected over time following administration, and fluorescence intensity in the collected blood samples was measured with the IVIS® Imaging System (Caliper Life Sciences Inc. (Xenogen Corp.)). The ratio of fluorescence intensity in blood samples collected 20 minutes after administration to fluorescence intensity in blood samples collected immediately after administration was determined as an indicator of blood retention.

Figure 6:
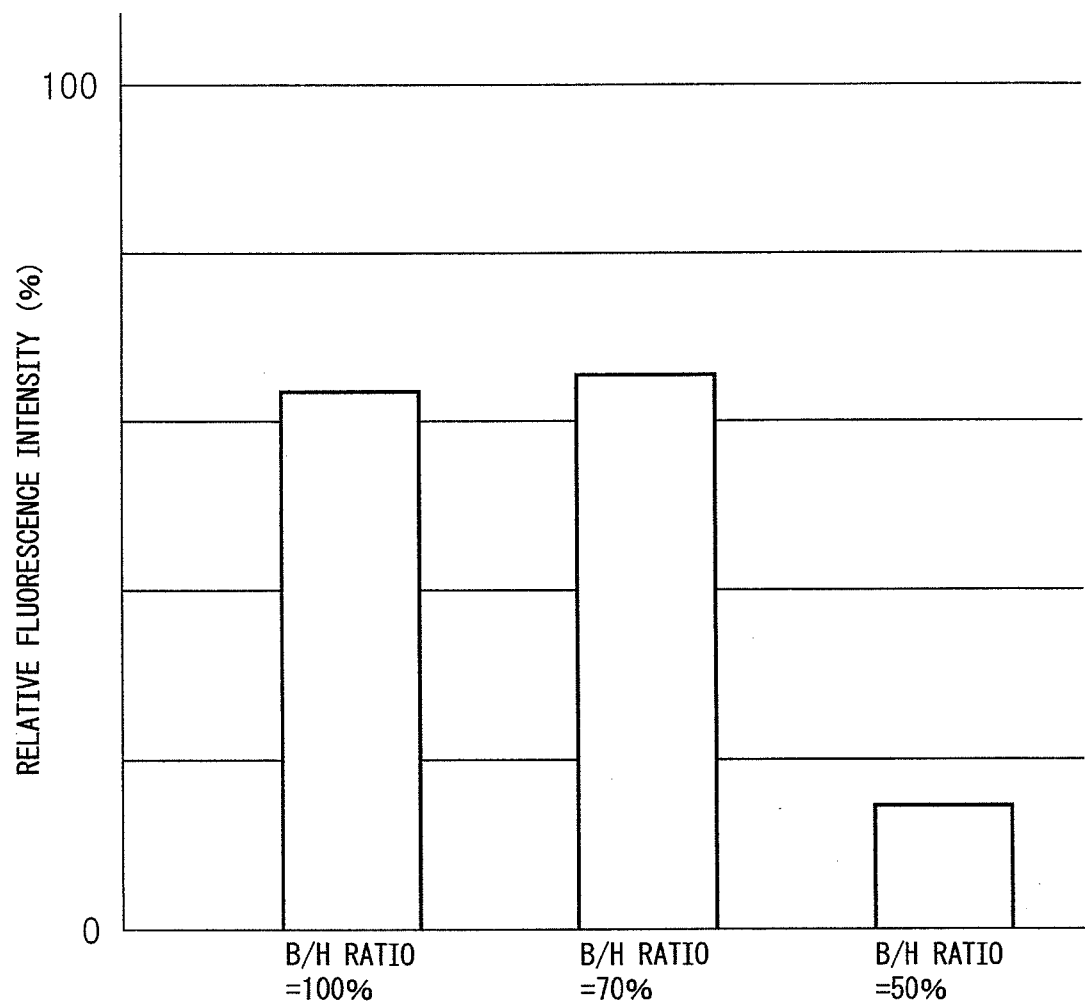
FIG. 6 is a graph showing blood retention of nucleic acid delivery compositions.

A graph representing indicators of blood retention (ratio of fluorescence intensity at 20 minutes after administration to fluorescence intensity immediately after administration) obtained for each B/H ratio is shown in FIG. 6. In the composition having a B/H ratio of 70%, fluorescence intensity attributable to nucleic acid was maintained at about the same level as that of the composition having a B/H ratio of 100% even at 20 minutes after administration. On the other hand, fluorescence intensity attributable to nucleic acid decreased in the composition having a B/H ratio of 50%.

(Observation of Nucleic Acid Expression in Tumor by Intravenous Infusion—Part 1)

Compositions (nucleic acid delivery compositions) (2OD, 200 µL) obtained using PEG-C3-PAsp(DET) for the block copolymer, using Venus pDNA for the nucleic acid, and making the B/H ratio 100% (block copolymer alone), 70% or 50% were each administered systemically by intravenous infusion to the aforementioned BxPC3 subcutaneously inoculated mice (using 1 animal per composition). The dosage was determined so that the dosage of nucleic acid per mouse was 20 µg. The tumors were excised 2 days after administration and used to prepare sections having a thickness of 10 µm. The sections were observed with a confocal laser scanning microscope (CLSM), and the expression level and expression site of Venus were examined and used as an indicator of effectiveness of nucleic acid expression by nucleic acid delivery. Furthermore, cell nuclei and vascular endothelial cells from the same sections were also immunostained for use as reference Venus expression sites, and those sites were also observed.

In addition, a control experiment was also carried out by administering the compositions and observing by CLSM in the same manner as described above using 10 mM HEPES buffer.

CLSM micrographs of the tumor tissue sections obtained for each B/H ratio are shown in FIGS. 7(a) to 7(d). In these CLSM micrographs, blue color indicates cell nuclei, red color indicates vascular endothelial cells, and green color indicates Venus expression sites. In contrast to hardly any Venus expression sites being observed in the control (HEPES buffer) (FIG. 7(a)) and those compositions having B/H ratios of 100% (FIG. 7(b)) and 50% (FIG. 7(c)), expression of Venus was observed even in cells at a distance from blood vessels in the composition having a B/H ratio of 70% (FIG. 7(d)).

(Observation of Nucleic Acid Expression in Tumor by Intravenous Infusion—Part 2)

A composition (nucleic acid delivery compositions) (2OD, 200 µL) obtained using PEG-C3-PAsp(DET) for the block copolymer, using sFlt-1 pDNA for the nucleic acid, and making the B/H ratio 70% was administered systemically by intravenous infusion to the aforementioned BxPC3 subcutaneously inoculated mice (using 1 animal per composition). The dosage was determined so that the dosage of nucleic acid per mouse was 20 µg. The tumors were excised 2 days after administration and used to prepare sections having a thickness of 10 µm followed by immunostaining of vascular endothelial cells. The vascular endothelial cell marker PECAM-1 and fluorescent labeled secondary antibody were used for immunostaining. In addition, cell nuclei and vascular endothelial cells from the same sections were also immunostained for use as reference sFlt-1 expression sites. The stained sections were observed with a confocal laser scanning microscope (CLSM), and the expression level and expression site of sFlt-1 were examined and used as an indicator of effectiveness of nucleic acid expression by nucleic acid delivery.

In addition, a control experiment was also carried out by administering the compositions, immunostaining the sections and observing by CLSM in the same manner as described above using 10 mM HEPES buffer instead of the nucleic acid delivery composition.

A CLSM micrograph of a tumor tissue section obtained for the control (HEPES buffer) is shown in FIG. 8(a), and a CLSM micrograph of a tumor tissue section obtained for the nucleic acid delivery composition having a B/H ratio of 70% is shown in FIG. 8(b). In these CLSM micrographs, blue color indicates cell nuclei, red color indicates vascular endothelial cells, and green color indicates sFlt-1 expression sites. In contrast to hardly any sFlt-1 expression sites being observed in the control (HEPES buffer), prominent expression of sFlt-1 was observed even in cells at a distance from blood vessels in the nucleic acid delivery composition having a B/H ratio of 70%.

(Measurement of Blood Vessel Density in Tumor by Intravenous Infusion)

Compositions (nucleic acid delivery compositions) (2OD, 200 µL) obtained using PEG-C3-PAsp(DET) for the block copolymer, using sFlt-1 pDNA for the nucleic acid, and making the B/H ratio 100% (block copolymer alone), 70% or 50% were each administered systemically by intravenous infusion to the aforementioned BxPC3 subcutaneously inoculated mice (using 3 animals per composition). Each animal was administered twice on day 0 and day 4 after the start of the experiment. The dosage was determined so that the dosage of nucleic acid per mouse was 20 µg. The tumors were excised 6 days after administration and used to prepare sections having a thickness of 10 µm followed by immunostaining of vascular endothelial cells. The vascular endothelial cell marker PECAM-1 and fluorescent labeled secondary antibody were used for immunostaining. The sections were observed with a confocal laser scanning microscope (CLSM), and seven CLSM micrographs were taken for each section. The resulting CLSM micrographs were analyzed with the LSM510 (Carl Zeiss Microimaging GmbH), the ratio of pixels emitting green color (equivalent to the ratio of vascular endothelial cells) was measured, and the average value of each section was determined in the form of microvessel density and used as an indicator of the inhibitory effect of nucleic acid delivery on vascularization.

In addition, in a comparative experiment, a composition (nucleic acid delivery compositions) obtained using PEG-C3-PAsp(DET) for the block copolymer, using Luc pDNA for the nucleic acid, and making the B/H ratio 70% was used, and administration, immunostaining and CLSM observation were carried out in the same manner as described above.

Moreover, in a control experiment, administration, immunostaining an CLSM observation were carried out in the same manner as described above using 10 mM HEPES buffer.

Examples of immunostained CLSM micrographs of tumor tissue obtained for each B/H ratio are shown in FIG. 9(a), while a graph indicating microvessel density as determined by analysis of the immunostained CLSM micrographs is shown in FIG. 9(b). In comparison with the control experiment (HEPES buffer), in contrast to changes in microvessel density not being observed for the composition using Luc pDNA (B/H ratio: 70%), in the composition using sFlt-1 pDNA, microvessel density decreased significantly particularly for the composition having a B/H ratio of 70%, and prominent inhibitory effects on vascularization were observed.

(Evaluation of Transfection Efficiency by Transpulmonary Administration)

Compositions (4OD, 50 µL) obtained using PEG-PAsp (DET) for the block copolymer, using Luc pDNA for the nucleic acid, and making the B/H ratio 100% (block copolymer alone), 75%, 50%, 25% or 0% (cationic polymer alone) were each administered by transpulmonary administration to the aforementioned Balb/c mice (using 5 animals per composition). Transpulmonary administration was carried out by spraying each of the compositions directly into the bronchi of the mice using a microsprayer (Microsprayer Model IA-IC-R, Penn Century, Inc.).

30 mg of cells from inside the lungs were harvested from the animals 24 hours after administration, and the cells were gently washed with PBS. 200 µL aliquots of cell lysis solution (Cell Culture Lysis Buffer: Promega Corp.) were added, and luciferase activity was determined by measuring photoluminescence intensity using a luciferase assay kit (Luciferase Assay System Kit: Promega Corp.) and an LB940 reader (Mithras Corp.) and used as an indicator of transfection efficiency. Furthermore, the amount of protein in the cell lysis solution was determined using the MicroBCA® Protein Assay Reagent Kit (Thermo Scientific Inc.).

Figure 10:
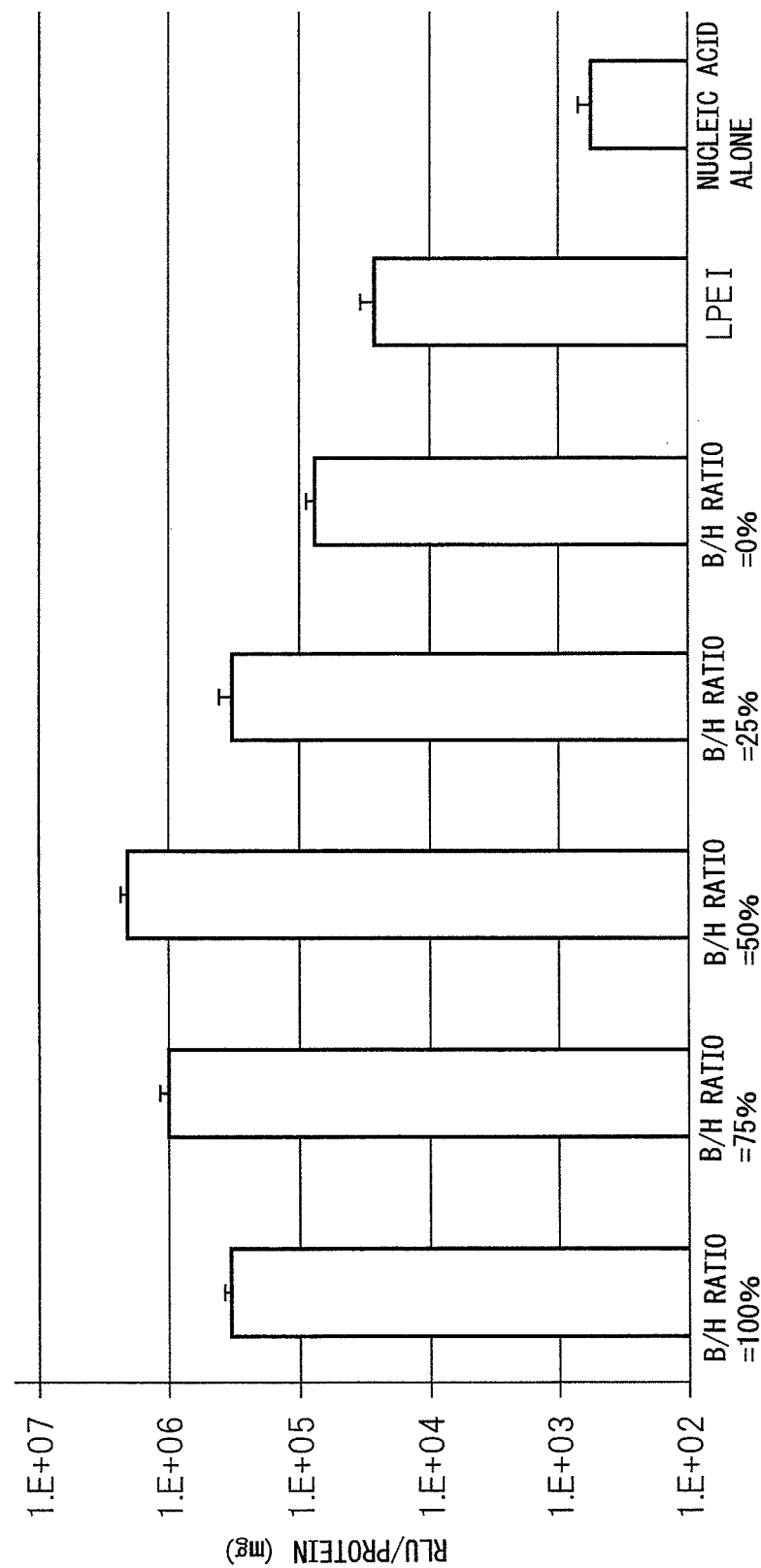
FIG. 10 is a graph showing the relationship between transfection efficiency and B/H ratio after pulmonary administration of compositions.

In addition, the commercially available gene transfection agent, linear polyethylene (LPEI, Exgen 500, Fermantas, Inc.) was administered followed by harvesting of lung cells and determination of luciferase activity using the same technique ("LPEI" in FIG. 10).

In addition, a solution obtained by dissolving 10 mg of Luc pDNA in 50 µl of 10 mM HEPES buffer solvent was administered in the same manner as a control followed by harvesting of lung cells and determination of luciferase activity ("nucleic acid alone" in FIG. 10).

A graph indicating the transfection efficiency of each composition is shown in FIG. 10. Each of the compositions having a B/H ratio of 75% and 50% clearly demonstrated improved transfection efficiency in comparison with the compositions having a B/H ratio of 100% (block copolymer alone) and B/H ratio of 0% (cationic polymer alone).

(Evaluation of Cytotoxicity by Transpulmonary Administration)

Lung tissue was harvested 4 hours after administration from Balb/c mice (using one animal per composition) that underwent transpulmonary administration in the same manner as described above using compositions (4OD, 50 µL) obtained using PEG-PAsp(DET) for the block copolymer, using Luc pDNA for the nucleic acid, and making the B/H ratio 100% (block copolymer alone), 50% or 0% (cationic polymer alone), following by staining the tissue with hematoxylin and eosin, and observing for the presence or absence of inflammation from optical (bright field?) micrographs.

In addition, Balb/c mice that did not undergo transpulmonary administration were observed for the presence or absence of inflammation using the same procedure as a control.

Optical micrographs obtained for each composition are shown in FIGS. 11(a) to 11(d). In contrast to inflammation (indicated with circles in the drawing) having been induced in the animal administered the composition having a B/H ratio of 0% (cationic polymer alone), there were no changes in lung tissue as compared with the control animal (FIG. 11(d)) in the lung tissue of the animal administered the composition having a B/H ratio of 50% (FIG. 11(b)) and the animal administered the composition having a B/H ratio of 100% (block copolymer alone, FIG. 11(c)), and hardly any inflammation was observed.

(Evaluation of Inflammatory Cytokine Expression by Transpulmonary Administration)

30 mg of cells from inside the lungs were harvested 4 hours after administration from Balb/c mice (using five animals per composition) that underwent transpulmonary administration in the same manner as described above using compositions (4OD, 50 µL) obtained using PEG-PAsp(DET) for the block copolymer, using Luc pDNA for the nucleic acid, and making the B/H ratio 100% (block copolymer alone), 50% or 0% (cationic polymer alone), following by measuring the expression levels of mRNA of inflammatory cytokines consisting of IL-6, TNF-α, Cox-2 and IL-10. The expression level of each mRNA was measured by quantitative PCR using TaqMan Gene Expression Assays and the ABI Prism 7500 Sequence Detector (Applied Biosystems Inc.). In addition, the measured mRNA expression levels were expressed in the form of a ratio to a value measured in a non-administered group (relative expression level).

In addition, transpulmonary administration and measurement of expression levels of inflammatory cytokine mRNA were carried out in the same manner as described above using 50 µl of 10 mM HEPES as a control.

The resulting relative expression levels of IL-6, TNF-α, Cox-2 and IL-10 mRNA are respectively shown in FIGS. 12(a) to 12(d). In contrast to expression levels of each of the inflammatory cytokines having increased considerably in comparison with the control group for the animals administered the composition having a B/H ratio of 0% (cationic polymer alone), in the animals administered the composition having a B/H ratio of 50% and the animals administered the composition having a B/H ratio of 100% (block copolymer alone), expression levels of each of the inflammatory cytokines were held to a low level.

INDUSTRIAL APPLICABILITY

According to the present invention, a superior nucleic acid delivery composition, nucleic acid delivery method and carrier composition thereof are provided that significantly suppress cytotoxicity while simultaneously demonstrating high nucleic acid transfection efficiency. This nucleic acid delivery composition and carrier composition can be preferably used as a pharmaceutical composition for gene therapy, for example, and the industrial value thereof is extremely high.

The invention claimed is:

1. A nucleic acid delivery composition for delivering a nucleic acid to a target cell or tissue, comprising: a block copolymer having an uncharged hydrophilic polymer segment and a cationic polymer segment; a second cationic polymer; and a nucleic acid, wherein the uncharged hydrophilic polymer segment of the block copolymer is a polyalkylene glycol segment, the cationic polymer segment of the block copolymer is a segment made of poly(amino acid) having amino groups at its side chains, and the second cationic polymer is poly(amino acid) having amino groups at its side chains, wherein the mol percentage (B/H ratio) of the cationic groups of the block copolymer to the total cationic groups of the block copolymer and the second cationic polymer is between 25% and 90%, wherein said block copolymer is selected from the group consisting of formulae (I) to (IV):

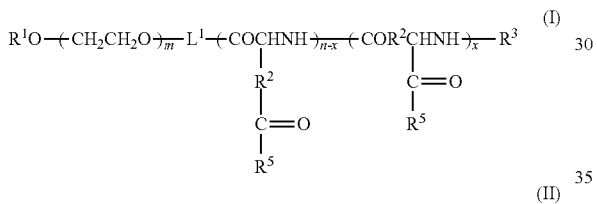

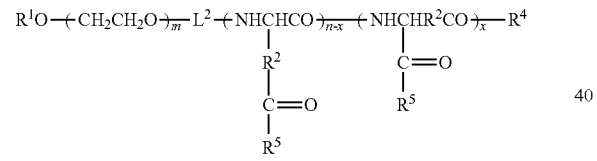

wherein, in formulae (I) and (II), $R^1$ represents a hydrogen atom or unsubstituted or substituted, linear or branched $C_{1-12}$ alkyl group, $R^2$ represents a methylene group or ethylene group, $R^3$ represents a hydrogen atom, protecting group, hydrophobic group or polymerizable group, $R^4$ is either the same as $R^5$ or represents an initiator residue, $R^5$ respectively and independently represent a hydroxyl group, oxybenzyl group or —NH—$(CH_2)_a$—X group, X respectively and independently represents a bulky amine compound residue having a pKa value of 7.4 or less, an amine compound residue containing one type or two or more types of a primary, secondary, tertiary or quaternary amine, or a non-amine compound residue, $L^1$ and $L^2$ respectively and independently represent a linking group, a represents an integer of 1 to 5, m represents an integer of 5 to 20,000, n represents an integer of 2 to 5,000, and x represents an integer of 0 to 5,000, provided that x is not greater than n;

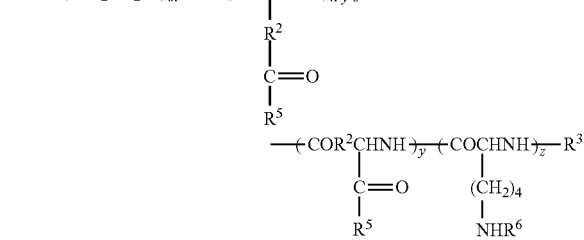

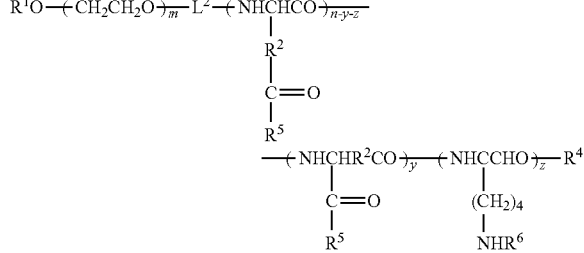

wherein, in formulae (III) and (IV), $R^1$ represents a hydrogen atom or unsubstituted or substituted, linear or branched $C_{1-12}$ alkyl group, $R^2$ represents a methylene group or ethylene group, $R^3$ represents a hydrogen atom, protecting group, hydrophobic group or polymerizable group, $R^4$ is either the same as $R^5$ or represents an initiator residue, $R^5$ respectively and independently represent a hydroxyl group, oxybenzyl group or —NH—$(CH_2)_a$—X group, provided that 85% or more of $R^5$ are —NH—$(CH_2)_a$—X groups, X respectively and independently represents a bulky amine compound residue having a pKa value of 7.4 or less, an amine compound residue containing one type or two or more types of a primary, secondary, tertiary or quaternary amine, or a non-amine compound residue, $L^1$ and $L^2$ respectively and independently represent a linking group, a represents an integer of 1 to 5, $R^6$ respectively and independently represents a hydrogen atom or protecting group, m represents an integer of 5 to 20,000, n represents an integer of 2 to 5,000, y represents an integer of 0 to 5,000 and z represents an integer of 0 to 5,000, provided that y+z is not greater than n; and wherein said second cationic polymer is selected from the group consisting of formulae (I') to (IV'):

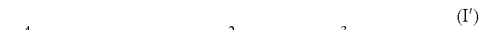

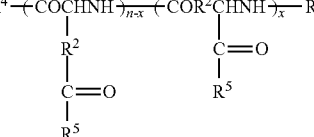

-continued

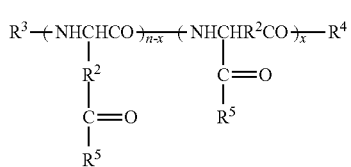
(II')

5 wherein, in formulae (I') and (II'), $R^2$, $R^3$, $R^4$, $R^5$, n and x have the same meanings as defined in formulae (I) and (II);

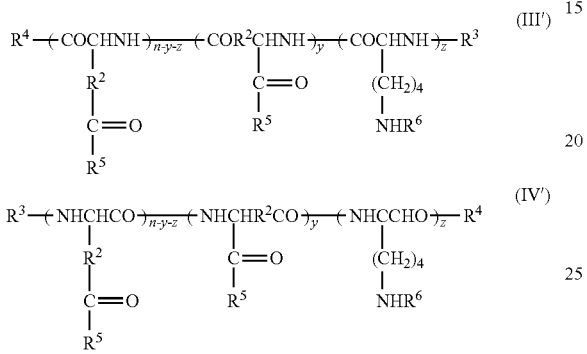

wherein, in formulae (III') and (IV'), $R^2$, $R^3$, $R^4$, $R^5$, $R^6$, n, x, y and z have the same meanings as defined in formulae (III) and (IV).

2. The nucleic acid delivery composition according to claim 1, wherein the mol ratio (N/P ratio) of the total cationic groups of the block copolymer and the cationic polymer to the phosphate groups of the nucleic acid is between 2 and 200.

3. The nucleic acid delivery composition according to claim 1, which is in a particulate form.

4. A carrier composition for delivering a nucleic acid to a target cell or tissue, comprising: a block copolymer having an uncharged hydrophilic polymer segment and a cationic polymer segment; and a second cationic polymer, wherein the uncharged hydrophilic polymer segment of the block copolymer is a polyalkylene glycol segment, the cationic polymer segment of the block copolymer is a segment made of poly(amino acid) having amino groups at its side chains, and the second cationic polymer is poly(amino acid) having amino groups at its side chains, and wherein the mol percentage (B/H ratio) of the cationic groups of the block copolymer to the total cationic groups of the block copolymer and the second cationic polymer is between 25% and 90%, wherein said block copolymer is selected from the group consisting of formulae (I) to (IV):

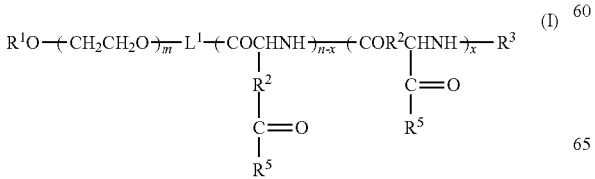
(I)

-continued

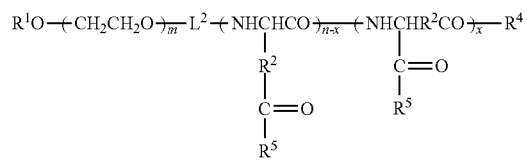
(II)

wherein, in formulae (I) and (II),
$R^1$ represents a hydrogen atom or unsubstituted or substituted, linear or branched $C_{1-12}$ alkyl group,
$R^2$ represents a methylene group or ethylene group,
$R^3$ represents a hydrogen atom, protecting group, hydrophobic group or polymerizable group,
$R^4$ is either the same as $R^5$ or represents an initiator residue,
$R^5$ respectively and independently represent a hydroxyl group, oxybenzyl group or —NH—$(CH_2)_a$—X group, provided that 85% or more of $R^5$ are —NH—$(CH_2)_a$—X groups,
X respectively and independently represents a bulky amine compound residue having a pKa value of 7.4 or less, an amine compound residue containing one type or two or more types of a primary, secondary, tertiary or quaternary amine, or a non-amine compound residue,
$L^1$ and $L^2$ respectively and independently represent a linking group,
a represents an integer of 1 to 5,
m represents an integer of 5 to 20,000,
n represents an integer of 2 to 5,000, and
x represents an integer of 0 to 5,000, provided that x is not greater than n;

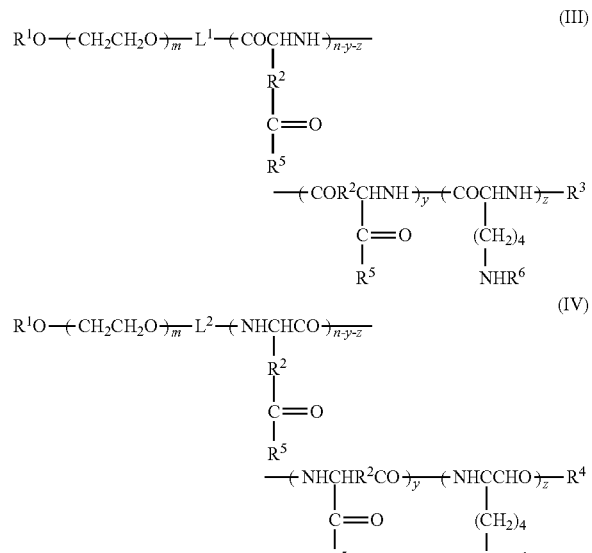

wherein, in formulae (III) and (IV),
$R^1$ represents a hydrogen atom or unsubstituted or substituted, linear or branched $C_{1-12}$ alkyl group,
$R^2$ represents a methylene group or ethylene group,
$R^3$ represents a hydrogen atom, protecting group, hydrophobic group or polymerizable group,
$R^4$ is either the same as $R^5$ or represents an initiator residue,
$R^5$ respectively and independently represent a hydroxyl group, oxybenzyl group or —NH—$(CH_2)_a$—X group, provided that 85% or more of $R^5$ are —NH—$(CH_2)_a$—X groups, X respectively and independently represents a bulky amine compound residue having a pKa value of 7.4 or less, an amine compound residue containing one type or two or more types of a primary, secondary, tertiary or quaternary amine, or a non-amine compound residue, $L^1$ and $L^2$ respectively and independently represent a linking group, a represents an integer of 1 to 5, $R^6$ respectively and independently represents a hydrogen atom or protecting group, m represents an integer of 5 to 20,000, n represents an integer of 2 to 5,000, y represents an integer of 0 to 5,000 and z represents an integer of 0 to 5,000, provided that y+z is not greater than n; and wherein said second cationic polymer is selected from the group consisting of formulae (I') to (IV'):

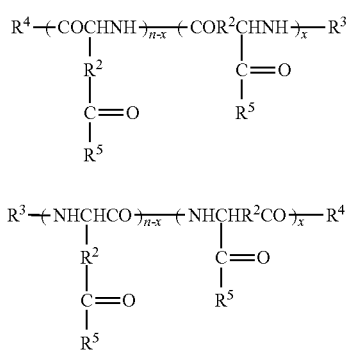

wherein, in formulae (I') and (II'), $R^2$, $R^3$, $R^4$, $R^5$, n and x have the same meanings as defined in formulae (I) and (II);

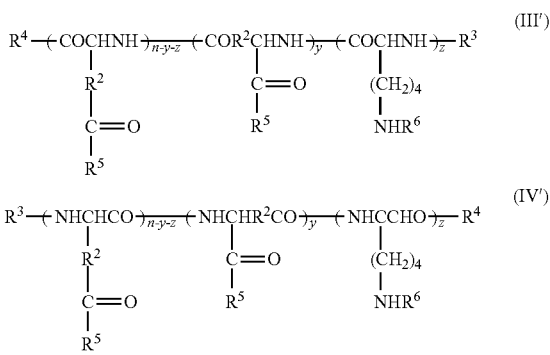

wherein, in formulae (III') and (IV'), $R^2$, $R^3$, $R^4$, $R^5$, $R^6$, n, x, y and z have the same meanings as defined in formulae (III) and (IV).

5. The carrier composition according to claim 4, which is in a particulate form.

6. A pharmaceutical composition for use in nucleic acid therapy, comprising a nucleic acid delivery composition according to claim 1.

7. A method for delivering a nucleic acid to a target cell or tissue, comprising contacting the target cell or tissue with a nucleic acid delivery composition according to claim 1.

8. A pharmaceutical composition for use in nucleic acid therapy, comprising a carrier composition according to claim 4.

* * * * *